United States Patent [19]
Wai Fei et al.

[11] Patent Number: 5,714,338
[45] Date of Patent: Feb. 3, 1998

[54] METHODS FOR DIAGNOSIS OF ALLERGY

[75] Inventors: David Tai Wai Fei, Belmont; John Lowe, Daly City; Paula Jardieu, San Francisco, all of Calif.

[73] Assignee: Genentech, Inc., South San Francisco, Calif.

[21] Appl. No.: 393,014

[22] PCT Filed: Dec. 9, 1994

[86] PCT No.: PCT/US94/14282

§ 371 Date: Feb. 27, 1995

§ 102(e) Date: Feb. 27, 1995

[87] PCT Pub. No.: WO95/16203

PCT Pub. Date: Jun. 15, 1995

Related U.S. Application Data

[63] Continuation-in-part of Ser. No. 165,436, Dec. 10, 1993, abandoned.

[51] Int. Cl.$^6$ .............. C07K 16/44; C12N 5/16; G01N 33/566
[52] U.S. Cl. .............. 435/7.24; 435/353; 436/513; 530/387.1; 530/387.3
[58] Field of Search .............. 435/7.1, 7.2, 7.21, 435/7.24, 7.8, 7.93, 240.2, 240.26, 325, 352, 353; 530/387.3, 387.1; 436/513

[56] References Cited

U.S. PATENT DOCUMENTS

| | | | |
|---|---|---|---|
| 4,559,310 | 12/1985 | Cantor et al. | 435/7.21 |
| 4,962,035 | 10/1990 | Leder et al. | 530/350 |
| 5,180,805 | 1/1993 | Gould et al. | 530/388.22 |

FOREIGN PATENT DOCUMENTS

| | | |
|---|---|---|
| WO 93/11437 | 6/1993 | WIPO. |
| WO 94/12876 | 6/1994 | WIPO. |

OTHER PUBLICATIONS

Carter et al. Proc. Nat. Acad. Sci (USA). 89:4285–4289, 1992.

Ishizaka, K and Ishizaka, T. In "Fundamental Immunology: Second Edition" W.E. Paul, ed. Raven Press, New York. pp. 867–888, 1989.

*Leukocyte Histamine Release Test, Clinical Documentation*, Roche Biomedical Laboratories (1990).

Baniyash and Eshhar, "Inhibition of IgE binding to mast cells and basophils by monoclonal antibodies to murine IgE" *European Journal of Immunology* 14:799–807 (1984).

Baniyash et al., "Anti-IgE monoclonal antibodies directed at the Fc$_\epsilon$ receptor binding site" *Molecular Immunology* 25(8):705–711 (1988).

Benveniste, J., "The human basophil degranulation test as an in vitro method for the diagnosis of allergies" *Clinical Allergy* 11:1–11 (1981).

Davis et al., "An epitope on membrane-bound but not secreted IgE: Implications in isotype-specific regulation" *Bio/Technology* 9:53–56 (1991).

Gilfillan et al., "Conservation of signal transduction mechanisms via the human FcεRIα after transfection into a rat mast cell line, RBL 2H3" *J. Immunol.* 149(7):2445–2451 (1992).

Gillespie et al., "Histamine Release from Human Leukocytes: Studies with Deuterium Oxide, Colcichine, and Cytochalasin B" *J. Clin. Invest.* 51:2941–2947 (1972).

Gleich & Hull, "Measurement of histamine: A quality control study" *J. Allergy Clin. Immunol.* 66:295–298 (1980).

Homburger & Katzmann, "Methods in Laboratory Immunology: Principles and interpretation of laboratory tests for allergy" *Allergy Principles & Practice*, Middleton et al., eds. pp. 554–572 (1992).

Hook et al., "Monoclonal antibodies defining epitopes on IgE" *Federation of American Societies for Experimental Biology* (71st Annual Meeting, Abstract #6008) (1987).

Ishizaka et al., "Mechanisms of passive sensitization III. Number of IgE Molecules and Their Receptor Sites on Human Basophil Granulocytes" *J. Immunol.* 111(2):500–511 (1973).

Knol et al., "Intracellular events in anti–IgE nonreleasing human basophils" *J. Allergy Clin. Immunol.* 90(1):92–103 (1992).

Levy & Osler, "Studies on the mechanisms of hypersensitivity phenomena XV. Enhancement of Passive Sensitization of Human Leukocytes by Heparin" *J. Immunol.* 99(6):1062–1067 (1967).

MacGlashan, Jr. & Botana, "Biphasic $Ca^{2+}$ responses in human basophils. Evidence that the initial transient elevation associated with the mobilization of intracellular calcium is an insufficient signal for degranulation" *J. Immunol.* 150(3):980–991 (Feb. 1993).

Marone et al., "IgG Anti–IgE from Atopic Dermatitis Induces Mediator Release from Basophils and Mast Cells" *J. Invest. Dermatol.* 93(2):246–252 (1989).

May et al., "Procedures for immunochemical study of histamine release from leukocytes with small volume of blood" *J. Allergy* 46(1):12–20 (1970).

(List continued on next page.)

*Primary Examiner*—Christina Y. Chan
*Assistant Examiner*—F. Pierre VanderVegt
*Attorney, Agent, or Firm*—Richard B. Love

[57] ABSTRACT

Provided are methods for the diagnosis of allergic disease wherein IgE specific for an allergen of interest is detected in a patient serum sample by using the patient serum sample to sensitize in the presence or absence of an IgE antagonist a mast cell or basophil host genetically engineered to display surface expression of a FcεRI subunit that is capable of mediating the host cells release of a pharmacological mediator upon induction with patient serum and allergen, challenging the sensitized host cells with the allergen of interest, and determining the presence or absence of IgE specific to the allergen of interest in the patient serum sample by comparing the release of the pharmacological mediator produced by host cells sensitized with patient serum in the presence of the IgE antagonist to the release of the pharmacological mediator produced by host cells sensitized with patient serum in the absence of the IgE antagonist.

15 Claims, 11 Drawing Sheets

OTHER PUBLICATIONS

Miller, Larry et al., "Expression of high-affinity binding of human immunoglobulin E by transfected cells" *Science* 244:334–336 (1989).

Mul et al., "An improved method for the purification of basophilic granulocytes from human blood" *J. Immunol. Methods* 149:207–214 (1992).

Nolte et al., "Diagnostic value of a glass fibre–based histamine analysis for allergy testing in children" *Allergy* 45:213–223 (1990).

Nolte et al., "A new glass microfibre–based histamine analysis for allergy testing in children" *Allergy* 42:366–373 (1987).

Peyret et al., "Antibodies to histamine: Specificity studies and radioimmunological assay" *J. Immunol. Methods* 90:39–45 (1986).

Prahl et al., "Basophil histamine release in children with adverse reactions to cow milk" *Allergy* 43:442–448 (1988).

Presta et al., "Humanization of an Antibody Directed Against IgE" *J. Immunol.* 151(5):2623–2632 (Sep. 1, 1993).

Pruzansky et al., "Dissociation of IgE from receptors on human basophils I. Enhanced Passive Sensitization for Histamine Release" *J. Immunol.* 131(4):1949–1953 (1983).

Rup and Kahn, "Identification of a mouse anti–rat IgE monoclonal antibody, 44.7b, which inhibits IgE binding to RBL cells" *International Archives of Allergy & Applied Immunology* 89(4):387–393 (1989).

Schellenberg et al., "Measurement of absolute amounts of antigen–specific human IgE by a radioallergosorbent test (RAST) elution technique" *J. Immunol.* 115(6):1577–1583 (1975).

Shimizu et al., "Human and rat mast cell high–affinity immunoglobulin E receptors: characterization of a putative $\alpha$–chain gene products" *Proc. Natl. Acad. Sci. USA* 85:1907–1911 (1988).

Siraganian et al., "Automated histamine analysis for in vitro allergy testing I. A method utilizing allergen–induced histamine release from whole blood" *J. Allergy Clin. Immunol.* 57(6):525–540 (1976).

Tai Wai Fei et al., "A novel bioactivity assay for monoclonal antibodies directed against IgE" *J. Immunol. Methods* 171:189–199 (1994).

van der Zee et al., "Discrepancies between the skin test and IgE antibody assays: Study of histamine release, complement activation in vitro, and occurrence of allergen–specific IgG" *J. Allergy Clin. Immunol.* 82(2):270–281 (1988).

van Toorenenbergen et al., "IgG4 and passive sensitization of basophil leukocytes" *International Archives of Allergy & Applied Immunology* 65:432–440 (1981).

Lindgren et al., "ACE–inhibitor–induced enhancement of spontaneous and IgE–mediated histamine release from mast cells and basophilic leukocytes and the modulatory effect of capsaicin sensitive nerves" *Chemical Abstracts* (abstract 165737y) 110(19):39 (1989).

Nolte et al., "Passive sensitization and histamine release of basophils. IgE and cellular factors regulating histamine release" *Chemical Abstracts* (abs 229451x) 113(25):560 (1990).

Sarfati et al., "The spontaneuous secretion of IgE by B lymphocytes from allergic individuals: a model to investigate the regulation of human IgE synthesis" *Chemical Abstracts* (abstract no. 228386v) 101(25):599 (1984).

Tharp et al., "IgE–mediated release of histamine from human cutaneous mast cells" *Chemical Abstracts* (abstract no. 158979j) 98(19):372 (1983).

Weyer et al., "Enhancement of the histamine–releasing activity of mouse monoclonal anti–human IgE antibody xb6–16 when present in aggregated or complexed forms" *Chemical Abstracts* (abstract no. 171581j) 110(19):630 (1989).

METHODS FOR DIAGNOSIS OF ALLERGY

This application is a §371 application of International Application No. PCT/US94/14282 filed Dec. 9, 1994, now inactive, which is a continuation-in-part application of U.S. Ser. No. 08/165,436 filed Dec. 10, 1993, now abandoned.

BACKGROUND OF THE INVENTION

1. Field of the Invention

This invention relates to the field of diagnosis of allergic disease, and to the screening of therapeutics for the treatment of allergic disease.

2. Description of the Background and Related Art

Three major techniques have been used in the diagnosis of allergic disease: skin tests, assays of IgE serum levels, and histamine release tests. Skin tests have represented the primary diagnostic tool in allergy since their introduction in 1865. The classical skin test in atopy is the Type I wheal and flare reaction in which antigen introduced into the skin leads to the release of preformed mediators, increased vascular permeability, local edema and itching. Such skin tests can provide useful confirmatory evidence for a diagnosis of specific allergy that has been made on clinical grounds. However, when improperly performed, skin tests can lead to falsely positive or negative results. The main limitation of the skin test is that a positive reaction does not necessarily mean that the disease is allergic in nature, as some non-allergic individuals have specific IgE antibodies that produce a wheal and flare reaction to the skin test without any allergic symptoms.

The IgE-mediated false positive phenomenon observed in skin tests is not observed in in vitro methods for assaying allergen-specific IgE in patient serum (see Homburger and Katzmann, "Methods in Laboratory Immunology: Principles and Interpretation of Laboratory Tests for Allergy," in *Allergy Principles and Practice*, Middleton et al., eds, Mosby, pub., 4th Edition, vol. 1, chap. 21, pp. 554–572 (1993)) Typically, allergen-specific IgE levels are measured by a radioallergosorbent test (RAST) wherein a patient's serum is incubated with antigen-coated sorbent particles, followed by detection of the specific. IgE bound to antigen with labelled antibody (see, e.g., Schellenberg et al., *J. Imunol.*, 115: 1577–1583 (1975)).

Total serum IgE levels are also used in the diagnosis of allergy. Total IgE levels can be measured by radioimmunoassay or immunometric assay methods as described by Homburger and Katzmann, supra. IgE levels are often raised in allergic disease and grossly elevated in parasitic infestations. When assessing children or adults for the presence of atopic disease, a raised level of IgE aids the diagnosis although a normal total IgE level does not exclude atopy. The determination of total IgE alone will not predict an allergic state as there are genetic and environmental factors which play an important part in the production of clinical symptoms. The value of serum IgE level in allergy diagnosis is also limited by the wide range of IgE serum concentrations in healthy individuals. The frequency distribution of IgE concentrations in healthy adults is markedly skewed with wide 95 percentile limits and a disproportionate number of low IgE values. Accordingly, in calculating the 95 percentile limits of normal IgE levels most investigators treat their data by logarithmic transformation, which yields upper limits for normal serum IgE that are very high when compared with arithmetic means. These high upper limits for normal serum IgE diminish the diagnostic value of the serum IgE test in screening for clinical allergy.

Histamine release tests provide a means to detect functional, allergen-specific IgE in patient serum. Typically, histamine release tests imitate the allergen-specific reaction as it occurs in the patient (see, e.g., under van der Zee et al., *J. Allergy Clin. Immunol.*, 82: 270–281 (1988)). This response has been generated in vitro by mixing a patient's blood with different allergens and later measuring the amount of histamine released during each of the subsequent allergic reactions. In vitro histamine release assays originally required the isolation of leukocytes from whole blood and/or various extractions of free histamine. Leukocyte histamine release tests were subsequently refined and automated to avoid cell isolation and histamine extraction (see, e.g., Siraganian et al., *J. Allergy Clin. Immunol.*, 57: 525–540 (1976)). At present, commercially available leukocyte histamine release testing kits permit up to 100 separate determinations with 2.5 ml of whole blood. However, blood samples cannot be stored for more than 24 hours prior to assay. In addition, the tests produce false positive results due to non-specific histamine release produced by toxicity of the allergen extracts or other factors. Also, a quality control study has reported considerable interlaboratory variability in the measurement of histamine (Gleich and Hull, *J. Allergy Clin. Immunol.*, 66: 295–298 (1980)).

In a minority of patients with allergic symptoms, positive skin tests and clearly detectable IgE antibodies, no in vitro histamine release can be obtained from the patients' basophil leukocytes with allergen. This phenomenon makes it impossible to interpret the results of a histamine release test if positive controls are not available and limits the usefulness of the test in diagnosing allergic disease. Levy and Osler, *J. Immunol.*, 99: 1062–1067 (1967) reported that leukocytes from only 20 to 30% of non-allergic individuals exhibit histamine release upon passive sensitization with allergen-specific IgE followed by allergen challenge in vitro. Ishizaka et al., *J. Immunol.*, 111: 500–511 (1973) expanded the usefulness of the test by showing that the incubation of leukocytes with deuterium oxide ($D_2O$) enhanced the histamine release induced by passive sensitization of leukocytes with anti-ragweed serum and challenge with ragweed antigen. Prahl et al., *Allergy*, 43: 442–448 (1988) reported the passive sensitization of isolated, IgE-deprived leukocytes from non-allergic individuals with serum from a non-releasing allergic patient followed by allergen-induced histamine release. However, the Prahl et al. method requires isolation of control leukocytes from the whole blood of a non-allergic donor followed by removal of IgE bound to the donor cells. Additionally, the Levy et al., Ishizaka et al., and Prahl et al. procedures are subject to the same histamine assay variation that limits the usefulness of the other histamine-release tests described above.

Accordingly, it is an object of the invention to provide a convenient, reproducible and widely applicable in vitro test for the diagnosis of allergic disease.

It is another object to provide an in vitro procedure for assaying the bioactivities of therapeutics for the treatment of allergic disease.

It is a further object to provide an in vitro procedure for screening IgE antagonists.

These and other objects will be apparent to those skilled in the art.

SUMMARY OF THE INVENTION

Accordingly, the invention provides for a method for an in vitro test for the diagnosis of allergic disease in a patient wherein an allergen-specific IgE in the patient's serum is detected by allowing the allergen-specific IgE to interact with (sensitize) the $Fc_\epsilon RI^+$ immune cells from a non-allergic donor both in the presence and absence of an IgE antagonist.

One aspect of the invention is a method for diagnosis of allergic disease in a patient comprising comparing release of a pharmacological mediator in a releasing mixture with release of a pharmacological mediator in a blocked releasing mixture, wherein the releasing mixture comprises a serum sample from the patient and a tissue sample from a naive donor, and wherein the blocked releasing mixture comprises a serum sample from the patient, a tissue sample from the naive donor, and an IgE antagonist, and wherein both the releasing mixture and the blocked releasing mixture are admixed with an allergen of interest.

The invention provides another in vitro test for the diagnosis of allergy wherein an allergen-specific IgE in a patient's serum is detected by allowing the allergen-specific IgE to interact, both in the presence and absence of an IgE antagonist, with a basophil or mast cell host genetically engineered to display surface expression of a $Fc_\epsilon RI$ α-subunit capable of effecting the host cell's release of a pharmacological mediator upon exposure to patient IgE and allergen. The allergen-specific IgE/$Fc_\epsilon RI$ interaction is assayed by adding the allergen and measuring the concomitant release of histamine or other pharmacological mediator. Any IgE antagonist is suitable for use in the assay, including IgE antagonists that compete with $Fc_\epsilon RI$ receptor for binding to IgE and IgE antagonists that compete with IgE for binding to $Fc_\epsilon RI$ receptor. The novel use of an IgE antagonist reduces false positive results due to non-specific release of pharmacological mediator or mediators.

One aspect of the invention is a method for diagnosis of allergic disease in a patient comprising (a) comparing release of a pharmacological mediator in a reaction mixture with release of the pharmacological mediator in a blocked reaction mixture, wherein
  (1) the reaction mixture and the blocked reaction mixture comprise cells that are the progeny of a common parent cell selected from the group consisting of: any mast cell host genetically engineered to display surface expression of a $Fc_\epsilon RI$ α-subunit that is capable of mediating the host cell's release of the pharmacological mediator upon induction by patient serum IgE and allergen, and any basophil cell host genetically engineered to display surface expression of a $Fc_\epsilon RI$ α-subunit that is capable of mediating the host cell's release of the pharmacological mediator upon induction by patient serum IgE and allergen,
  (2) the reaction mixture and the blocked reaction mixture each further comprises a portion of a single serum sample from the patient, the presence or absence in the serum sample of IgE specific for an allergen of interest being theretofore unknown,
  (3) the blocked reaction mixture further comprises an IgE antagonist, and
  (4) both the reaction mixture and the blocked reaction mixture are admixed with the allergen; and (b) determining, based on the comparison in step (a), the presence or absence in the serum sample of IgE specific for the allergen.

The invention also provides a method for an in vitro test for the bioactivity of an agent as an anti-allergy therapeutic and for the bioactivity of an agent as an IgE antagonist wherein the agent is assayed for its ability to block the interaction between allergen-specific IgE and $Fc_\epsilon RI$ receptor by contacting the allergen-specific IgE with $Fc_\epsilon RI^+$ immune cells in the presence or absence of the agent. The allergen-specific IgE/$Fc_\epsilon RI$ interaction is assayed by adding allergen-specific IgE/$Fc_\epsilon RI$ interaction is assayed by adding allergen and measuring the concomitant release of histamine or other pharmacological mediator.

One aspect of the invention is a method for assaying the bioactivity of an agent for blocking IgE-induced immune cell sensitization comprising comparing release of a pharmacological mediator in a releasing mixture with release of a pharmacological mediator in a blocked releasing mixture, wherein the releasing mixture comprises a tissue sample from a naive donor and a serum sample, and wherein the blocked releasing mixture comprises a tissue sample from the naive donor, a serum sample, and the agent, and wherein both the releasing mixture and the blocked releasing mixture are admixed with an allergen of interest.

Another aspect of the invention is a method for screening agents for the ability to inhibit immune cell degranulation. In this method, immune cells from a patient treated with the agent or donor immune cells preincubated with the agent in vitro are first mixed with allergen-specific IgE in the presence or absence of IgE antagonist, and the mixtures are then challenged with the allergen. The ability of IgE antagonist to reduce histamine release indicates the ability of the agent to inhibit immune cell degranulation.

DETAILED DESCRIPTION OF THE PREFERRED EMBODIMENTS

A. DEFINITIONS

Figure 1:
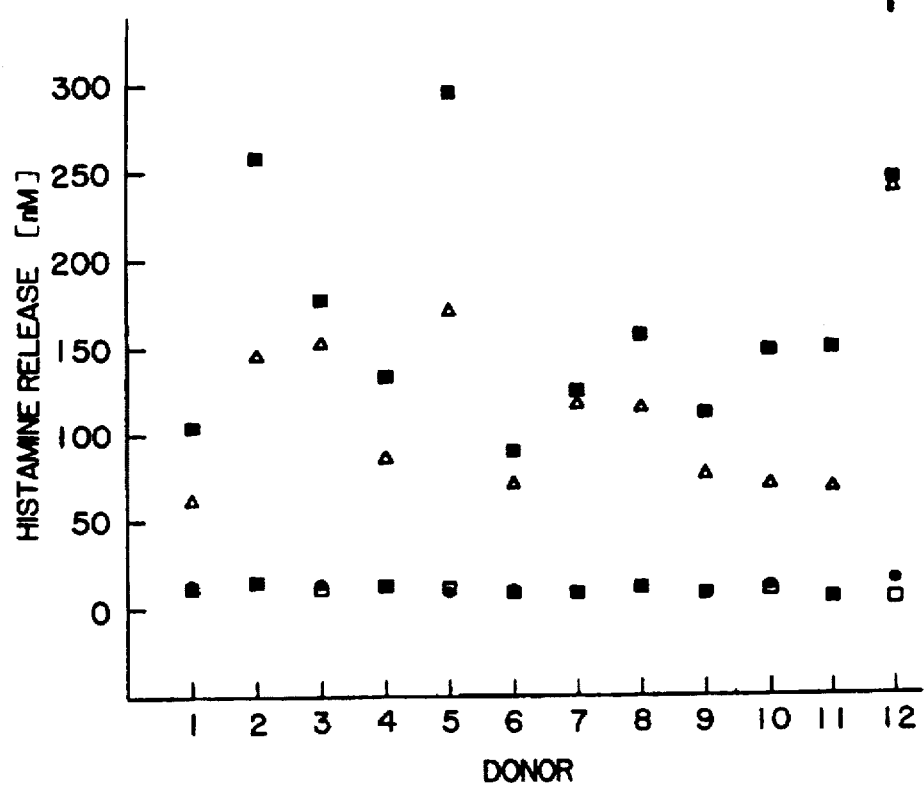
FIG. 1 is a graphic depiction of the inability of rhuMAbE25 to trigger histamine release. Blood samples from 12 naive donors were presensitized with 10% RSHP and challenged with HBSS/1% BSA, 0.1 µg/ml ragweed, 10 µg/ml MAE1, or 10 µg/ml rhuMAbE25 for 30 min at 37° C. The histamine released (nM) into the supernatants of the various reaction mixtures is shown as follows: HBSS/1% BSA mixtures are identified as open squares, ragweed mixtures are identified as filled squares, MAE1 mixtures are identified as open triangles, and rhuMAbE25 mixtures are identified as filled circles.

The term "IgE antagonist" as used herein denotes a compound capable of disrupting or blocking the interaction between IgE and the high affinity receptor $Fc_\epsilon RI$ on immune cells or genetically engineered cells such that the cells do not release a pharmacological mediator or mediators in response to allergen stimulus. Preferably, the IgE antagonist is also characterized by its inability to induce immune cell or genetically engineered cell release of a particular pharmacological mediator or mediators. antagonists include anti-IgE antibody of any immunoglobulin type, such as IgG, IgA, IgM, IgD and IgE, and fragments thereof, soluble $Fc_\epsilon RI$ receptor and fragments thereof, anti-$Fc_\epsilon RI$ antibody and fragments thereof, IgE variants and fragments thereof, IgE-binding peptides, $Fc_\epsilon RI$ receptor-binding peptides, and non-proteinaceous small molecules capable of binding to IgE or competing with IgE for binding to $Fc_\epsilon RI$ receptor.

"Anti-IgE antibody" as used herein is defined as any antibody capable of binding to IgE such that the bound IgE's ability to interact with $Fc_\epsilon RI$ receptor is impaired or eliminated.

"Anti-IgE antibody fragment" as used herein is defined as any portion of an anti-IgE antibody molecule that is capable of binding to IgE such that the bound IgE's ability to interact with $Fc_\epsilon RI$ receptor is impaired or eliminated.

"Soluble $Fc_\epsilon RI$ receptor" as used herein is defined as any molecule comprising the IgE binding site in the extracellular domain (exodomain) of the $Fc_\epsilon RI$ α chain, wherein the molecule is capable of binding to IgE such that the bound IgE's ability to interact with $Fc_\epsilon RI$ receptor is impaired or eliminated.

The term "IgE variant" as used herein is defined as any IgE molecule with an alteration, such as an amino acid substitution or substitutions and/or an amino acid deletion or deletions, which reduces or eliminates the ability of the IgE molecule to sensitize immune cells and wherein the altered IgE molecule is capable of competing with IgE for binding to $Fc_\epsilon RI$ receptor.

The terms "IgE variant fragment" and "fragment of an IgE variant" as used herein are defined as any fragment of an IgE variant that is capable of competing with IgE for binding to $Fc_\epsilon RI$ receptor.

The term "IgE-binding peptide" as used herein is defined as any peptide, including soluble $Fc_\epsilon RI$ receptor and anti-IgE antibodies and fragments thereof, that is capable of competing with $Fc_\epsilon RI$ receptor for binding to IgE.

The term "$Fc_\epsilon RI$ receptor-binding peptide" as used herein is defined as any peptide, including IgE variants and other antibodies and fragments thereof, capable of competing with IgE for binding to $Fc_\epsilon RI$ receptor.

The term "allergen" as used herein refers to any antigen, such as pollen, ragweed, dust mite, and cow milk antigens, capable of generating a Type I hypersensitivity reaction in a patient upon the patient's second or subsequent exposure to the antigen.

The term "pharmacological mediator" as used herein denotes any compound that is released by an $Fc_\epsilon RI^+$ immune cell and that is capable of mediating an inflammatory response, such as histamine, leukotrienes, prostaglandins and platelet activating factor.

The term "$Fc_\epsilon RI^+$ immune cell" as used herein is intended to refer to a cell expressing the $Fc_\epsilon RI$ high affinity receptor and which is capable of releasing a pharmacological mediator or mediators upon IgE-induced sensitization and exposure to an antigen of interest, such as mast cells and basophils.

The term "genetically engineered" as used herein refers to cells which have been altered from their native state by the introduction of exogenous or additional endogenous DNA, along with the progeny of such altered cells. Examples of genetically engineered mast cells include a mast cell that expresses an exogenous DNA encoding a $Fc_\epsilon RI$ α-chain that is heterologous to the host cell, a mast cell that expresses an exogenous DNA encoding a $Fc_\epsilon RI$ α-chain that is homologous to the host cell, and a mast cell containing an exogenous DNA that upregulates the host cell's expression of endogenous DNA encoding $Fc_\epsilon RI$ α-chain. Examples of genetically engineered basophils include a basophil that expresses an exogenous DNA encoding a $Fc_\epsilon RI$ α-chain that is heterologous to the host cell, a basophil that expresses an exogenous DNA encoding a $Fc_\epsilon RI$ α-chain that is homologous to the host cell, and a basophil containing an exogenous DNA that upregulates the host cell's expression of endogenous DNA encoding $Fc_\epsilon RI$ α-chain.

The terms "patient serum" and "serum sample from a patient" as used herein are defined as any fraction of the patient's blood which contains IgE and lacks $Fc_\epsilon RI^+$ immune cells.

The terms "serum sample" and "serum comprising IgE specific to an allergen of interest" as used herein refer to any preparation containing IgE capable of sensitizing $Fc_\epsilon RI^+$ immune cells such that challenge of the sensitized $Fc_\epsilon RI^+$ immune cells with the allergen of interest induces the release of a pharmacological mediator or mediators.

The terms "donor" "naive donor" "healthy donor" and "non-allergic donor" are used interchangeably herein and are intended to refer to an individual with no allergy to an allergen of interest.

The terms "tissue sample from a naive donor" and "donor tissue" as used herein are defined as any tissue, including lung tissue, whole blood, and blood fractions, taken from the naive donor which comprises $Fc_\epsilon RI^+$ immune cells.

The terms "blood sample from a naive donor" and "donor blood" as used herein are defined as any blood fraction, including whole blood, taken from the naive donor which comprises $Fc_\epsilon RI^+$ immune cells.

The terms "releasing mixture", "sensitized mixture", "sensitized immune cells" and "sensitized donor blood" as used herein refer to a mixture of patient serum or other serum sample and donor tissue wherein any allergen-specific IgE present in the patient serum or serum sample is permitted to interact with $Fc_\epsilon RI^+$ immune cells present in the donor tissue.

The terms "blocked releasing mixture" and "blocked sensitization mixture" as used herein refer to a mixture of patient serum or other serum sample, donor tissue, and an agent that is an IgE antagonist or is a candidate IgE antagonist or candidate anti-allergy therapeutic. In the case of an IgE antagonist, the agent is preferably present in sufficient concentration to reduce the interaction between any allergen-specific IgE present in the patient serum or serum sample and $Fc_\epsilon RI^+$ immune cells present in the donor tissue. In the case of a candidate IgE antagonist or candidate anti-allergy therapeutic, the agent is preferably present in sufficient concentration to permit assay of the agent's ability to disrupt or block IgE interaction with $Fc_\epsilon RI^+$ immune cells. The term "bioactivity of an agent for blocking IgE-induced immune cell sensitization" as used herein is defined as the agent's ability to disrupt or block IgE interaction with $Fc_\epsilon RI^+$ immune cells. The definition includes bioactivities that block or disrupt IgE/immune cell interaction by competing with $Fc_\epsilon RI$ for binding to IgE and bioactivities that block or disrupt IgE/immune cell interaction by competing with IgE for binding to $Fc_\epsilon RI$.

The term "candidate anti-allergy therapeutic" as used herein is defined as any agent that is to be evaluated for use in the treatment of allergic disease.

The term "candidate IgE antagonist" as used herein is defined as any agent that is to be evaluated for use as an IgE antagonist.

The terms "IgE interaction with $Fc_\epsilon RI^+$ immune cells", "IgE-induced immune cell sensitization", "$Fc_\epsilon RI^+$ immune cell sensitization", "immune cell sensitization", and "IgE interaction with $Fc_\epsilon RI$ receptor" as used herein are defined as the binding of allergen-specific IgE to immune cell $Fc_\epsilon RI$ receptor such that subsequent binding of allergen to $Fc_\epsilon RI$ receptor-bound IgE induces immune cell release of pharmacological mediator or mediators.

B. GENERAL METHODS

I. Detection of Allergen-Specific IgE with Naive $Fc_\epsilon RI^+$ Cells

In one aspect, the invention provides methods for the diagnosis of allergic disease. In general, the methods involve the detection of allergen-specific IgE in the serum of an allergic patient using $Fc_\epsilon RI^+$ immune cells. More specifically, an allergen-specific IgE in the allergic patient's serum is detected by allowing the allergen-specific IgE to interact with (sensitize) the open $Fc_\epsilon RI$ receptor on basophils and/or mast cells both in the presence and absence of an IgE antagonist. The allergen-specific IgE/$Fc_\epsilon RI$ interaction is assayed by adding the allergen and measuring the concomitant release of histamine or other pharmacological mediator. Since the IgE antagonist blocks IgE/$Fc_\epsilon RI$ interaction, a lower histamine concentration in the reaction mixture containing IgE antagonist indicates the presence of allergen-specific IgE in the patient's serum. Although histamine serves as an example of a pharmacological mediator that can be used to indicate allergen-induced, IgE-mediated immune cell release of compounds involved in an inflammatory response in much of the following discussion, it will be appreciated that the invention encompasses the use of any such pharmacological mediator, including leukotrienes, prostaglandins and platelet activating factor, in the methods defined, discussed and claimed herein.

a. Preparation of Naive $Fc_\epsilon RI^+$ Immune Cells

In one embodiment, the method involves contacting a patient's serum with $Fc_\epsilon RI^+$ immune cells from a naive donor. Any tissue sample from a naive donor that comprises $Fc_\epsilon RI^+$ immune cells capable of releasing a pharmacological mediator or mediators in response to IgE sensitization and allergen challenge can be used to detect the presence of allergen-specific IgE in a patient's serum. For example, a tissue sample comprising basophils can be used. Since approximately 15% of individuals have basophils which do not release histamine in vitro, potential donors should be screened for basophil histamine releasability that is adequate for use in the present method. Preferably, donor basophils presensitized with allergen-specific IgE release greater than 7%, and more preferably greater than 10%, of the total cellular histamine upon allergen challenge. Donors can be screened for histamine release with any allergen and corresponding IgE according to the donor screening method for ragweed-induced histamine release described in the Examples below. The potential pool of donors with acceptable releasability is increased by incubating the donor cells in the presence of deuterium oxide ($D_2O$). As shown below in the Examples, the presence of $D_2O$ in the incubation medium enhances allergen-induced histamine release. $D_2O$ can be effectively used at a final concentration in the incubation medium of about 10% to 50%, and preferably about 20% to 40%, and most preferably about 33%.

In a preferred embodiment, a whole blood sample from the naive donor is used. The use of whole blood advantageously minimizes the manipulation of basophils prior to assay and avoids any disruption of cell function caused by cell isolation procedures. The whole blood sample can be anti-coagulated and diluted with a buffered salt solution prior to use in the assay. Since the presence of $Ca^{2+}$ in the incubation medium has a substantial effect on histamine release (MacGlashan and Botana, *J. Imunol.*, 150: 980–991 (1993)), it is preferred that the dilution buffer contains $Ca^{2+}$. Alternatively, the dilution buffer can contain $Mg^{2+}$ to increase histamine release as described in the Examples below. The dilution of a blood sample in Hank's balanced salt buffer (HBSS), containing both 1.3 mM $Ca^{2+}$ and 0.9 mM $Mg^{2+}$, at a ratio of about 1:2 to 1:10, and more preferably about 1:5 to 1:7, provides a good environment for histamine release.

Alternatively, isolated leukocytes from the naive donor can be used. The leukocytes can be isolated and prepared according to the method of Gillespie et al., *J. Clin. Invest.*, 51: 2941–2947 (1972).

In another embodiment, the numbers of open $Fc_\epsilon RI$ receptors in donor cells can be increased by removal of IgE from the basophil cell surface. This technique increases the pool of potential donors with adequate receptor numbers for the assay. Bound IgE can be removed from the basophil cell surface by washing the blood and by suspending the blood cells in phosphate buffer (pH 3.6) for about 5 minutes at 4°

C. as described by Prahl et al., supra, or by lactic acid wash as described by Pruzansky et al., *J. Immunol.*, 13: 1949–1954 (1983).

In a further embodiment, a donor tissue sample comprising mast cells can be used. Tissue samples containing mast cells can be obtained from a naive donor's lung tissue. The lung tissue can be obtained and prepared as a cell suspension as described in Marone et al., *J. Invest. Dermatol.*, 93: 246–252 (1989).

b. Preparation of Patient Serum

Any fraction of a patient's blood which contains IgE and/or lacks $Fc_\epsilon RI^+$ immune cells is suitable for use in the diagnosis of allergy according to the present method. Since it is easily obtained, a patient serum sample is a convenient fraction for analysis.

c. Sensitization of Naive $Fc_\epsilon RI^+$ Immune Cells with Patient Serum

The patient's serum is added to the naive donor tissue sample with or without IgE antagonist to form a blocked sensitization mixture or a sensitized mixture, respectively. When the donor tissue is a blood sample, the desirable ratio of patient serum to donor blood in the mixture will vary according to the fraction of the donor blood and the dilution thereof to be used and the dilution of the patient serum to be tested. In the case of donor whole blood diluted 1:7 with HBSS/1% BSA mixed with undiluted patient serum, a suitable ratio of donor blood to patient serum is about 2:1 to 20:1, and preferably about 4:1 to 15:1, and more preferably about 9:1.

At least two mixtures of patient serum/naive donor $Fc_\epsilon RI^+$ immune cells are compared in parallel. In one mixture, IgE antagonist is used to block the binding of patient serum IgE to naive donor $Fc_\epsilon RI^+$ immune cells. In a second mixture, the patient serum is exposed to naive donor $Fc_\epsilon RI^+$ immune cells in the absence of IgE antagonist. In a preferred embodiment, an IgE antagonist that binds to IgE is used in a range of concentrations in patient serum/donor tissue mixtures to titer the allergen-specific IgE in the patient serum. The analysis of the effects of a range of IgE antagonist concentrations provides a powerful tool in assessing the severity of the patient's allergic condition. Optionally, serum samples known to contain allergen-specific IgE are also tested with or without IgE antagonist according to the present method in order to provide negative and positive controls, respectively.

The desired concentration of IgE antagonist in the blocked sensitization mixture will vary according to the type of IgE antagonist used. In the case of an IgE antagonist that competes with $Fc_\epsilon RI$ receptor for binding to IgE, the preferred concentration of the IgE antagonist depends on the relative affinities of the IgE antagonist and $Fc_\epsilon RI$ receptor for IgE. When total blockade of IgE/$Fc_\epsilon RI$ receptor interaction is desired, it is preferable to use an IgE antagonist concentration that is sufficient for saturation of the IgE present in the blocked sensitization mixture. In the case of an IgE antagonist that competes with IgE for binding to $Fc_\epsilon RI$ receptor, the preferred concentration of the IgE antagonist depends on the relative affinities of IgE and the IgE antagonist for $Fc_\epsilon RI$ receptor. When total blockade of IgE/$Fc_\epsilon RI$ receptor interaction is desired, it is preferable to use an IgE antagonist concentration that is sufficient for saturation of the $Fc_\epsilon RI$ receptor present in the blocked sensitization mixture.

When an anti-IgE monoclonal antibody is used as the IgE antagonist and when blood is used as the source of naive donor $Fc_\epsilon RI^+$ immune cells, a useful range of antibody concentrations in the patient serum/donor blood mixture is preferably about 0.001 to 10 µg/ml, and more preferably about 0.005 to 5 µg/ml, and still more preferably about 0.01 to 2 µg/ml.

IgE antagonist can be mixed with the donor tissue either prior to or at the same time that the patient serum is added to the donor tissue mixture. Alternatively, the patient serum can be premixed with IgE antagonist and then mixed with donor tissue.

The donor tissue/patient serum mixtures are incubated under conditions suitable for IgE binding to $Fc_\epsilon RI$ receptor. In the case of donor blood/patient serum mixtures, preferred conditions consist of about 2 hours of incubation at approximately 37° C. in a humidified, 5% $CO_2$ incubator as described in the Examples below.

d. Allergen Challenge of Sensitized $Fc_\epsilon RI^+$ Immune Cells

Following incubation, aliquots of the sensitized mixtures and blocked sensitization mixtures are challenged with the allergen of interest. Preferably, aliquots of the sensitized mixtures and blocked sensitization mixtures of approximately 50 to 200 µl, or more preferably 100 to 150 µl, in size are used for allergen challenge. The aliquots of sensitized mixtures and blocked sensitization mixtures can be placed in the wells of microtiter plates for convenient reaction with allergen and analysis. A sufficient amount of the allergen is added to each well and the reaction mixture can be diluted with a buffer suitable for histamine release. The amount of allergen needed depends upon the concentration of IgE-bound $Fc_\epsilon RI$ receptor and the allergen-specific binding affinity of the IgE. Although an excess of allergen can be used in the reaction mixture, higher concentrations of allergen may cause non-specific induction of histamine release. Allergen concentrations of about 0.01 µg/ml to 100 µg/ml, and more preferably about 0.05 µg/ml to 15 µg/ml, and still more preferably about 0.1 µg/ml to 1 µg/ml, are suitable for reacting most allergens with sensitized immune cells in the present assay.

The incubation conditions for the allergen reaction mixtures are chosen to allow the induction of histamine release. In a preferred embodiment, the reaction mixture is incubated for about 20 to 30 minutes at a temperature of at least 32° C., and more preferably at least 37° C.±1° C.

e. Assay of Histamine Release

The histamine release in the allergen reaction mixtures can be stopped by sharply lowering the temperature in the reaction vessels by any convenient method such as placing the microtiter plates on ice. For each sample, total cellular histamine can be measured by disrupting the cells, separating histamine from cellular debris and assaying the separated histamine. Cells can be disrupted by any convenient method, such as sonication, Manton-Gaulin press or osmotic pressure and freeze thawing, and the histamine is easily separated from cellular debris, e.g., by filtration or centrifugation. The concentration of histamine can be determined by a number of methods, including spectrophotofluorimetry as described in Nolte et al., *Allergy*, 42: 366–373 (1987), radioimmunoassay as described by Peyret et al., *J. Immunol. Methods*, 90: 39–45 (1986), and enzyme immunoassays such as a binding competition immunoassay wherein histamine competes with histamine-conjugated enzyme for binding to antibody fixed to a solid support, followed by detection of bound enzyme with a chromogenic substrate. As described in the Examples below, a histamine immunoassay kit available from AMAC, Inc., Westbrook, Me. can be used to measure histamine levels in the present method.

In a further embodiment of the invention, histamine concentration can be measured by performing the histamine releasing reactions in the presence of glass fibers followed by detection of the histamine bound to the glass fibers. Microtiter plates can be layered with glass microfibers as described in Nolte et al. To avoid the trapping of blood cells in the microfibers, Pipes-AMC can be added to the wells according to the method of Nolte et al. Next, donor blood and patient serum with or without IgE antagonist are added to the wells, followed by reaction with allergen as in the methods described above. Interfering substances can be separated from the histamine bound to the microfibers by washing the plates. Histamine is released from the microfibers by addition of a suitable solvent such as the $HClO_4$/o-phthaldialdehyde mixture described in Nolte et al., and the histamine content can be determined by any of the methods described above.

Lastly, the percent inhibition of histamine release caused by the IgE antagonist is calculated. The percent inhibition caused by a particular concentration of antagonist can be determined by subtracting the amount of histamine released in the presence of IgE antagonist from the amount of histamine released in the absence of IgE antagonist, and dividing the difference by the amount of histamine released in the absence of IgE antagonist. The ability of the IgE antagonist to reduce histamine release indicates the presence of allergen-specific IgE in the patient's serum and thus identifies allergic reaction to the particular allergen. The amount of IgE antagonist needed to reduce histamine release is an indication of the clinical intensity and severity of allergic symptoms.

II. Kit for Detection of Allergen-Specific IgE in Patient Serum with Naive $Fc_\epsilon RI^+$ Immune Cells The testing system of the present invention can be supplied in the form of a kit, the components of which comprise a vial containing naive donor $Fc_\epsilon RI^+$ immune cells, a vial containing an IgE antagonist, and one or more vials containing allergen(s) of interest; The naive donor $Fc_\epsilon RI^+$ immune cells can be provided in the form of whole blood, a blood fraction, a washed leukocyte cell suspension, or a mast cell suspension derived from a naive donor and are conveniently stored in a refrigerated container. The kit can also include a vial containing a buffered salt solution suitable for promoting the release of pharmacological mediator(s) in the sensitized releasing mixtures as described in Section Ia above.

Optionally, one or more vials containing IgE specific for the allergen(s) of interest are provided as a positive control. The positive control allergen-specific IgE is derived from the same animal species as the patient to be tested. The positive control allergen-specific IgE can be supplied in known concentrations to facilitate construction of a standard curve useful for titering the allergen-specific IgE in patient serum.

In one embodiment, the kit includes vials containing reagents used in the analysis of pharmacological mediator(s) released by the donor naive $Fc_\epsilon RI^+$ immune cells.

In another embodiment, the kit includes a package label or package insert providing instructions as to the use of the kit in any of the methods described in Section I above.

III. Detection of Allergen-Specific IgE in Patient Serum with Genetically Engineered Cells The invention further encompasses a method for detecting allergen-specific IgE in a patient serum sample by exposing the patient serum to a mast cell or basophil genetically engineered to display surface expression of a $Fc_\epsilon RI$ α-chain capable of mediating the host cell's release of a pharmacological mediator or mediators upon sensitization of the genetically engineered cell with allergen-specific IgE in the patient's serum and exposure to allergen. In this system, the $Fc_\epsilon RI$ α-chain expressed by the genetically engineered mast cell host or basophil host is capable of binding to any IgE in the patient's serum. In addition, the $Fc_\epsilon RI$ α-chain is capable of operating in the host cell's pharmacological mediator releasing effector function. The $Fc_\epsilon RI$ α-chain is expressed on the host cell surface in a functional IgE receptor complex and in sufficient numbers such that allergen-induced cross-linking of patient IgE-bound $Fc_\epsilon RI$ α-chain triggers mediator release. An allergen-specific IgE in the allergic patient's serum is detected by allowing the allergen-specific IgE to interact with the $Fc_\epsilon RI$ receptor α-chain on genetically engineered mast cell or basophil hosts both in the presence and absence of an IgE antagonist. The allergen-specific IgE/$Fc_\epsilon RI$ α-chain interaction is assayed by adding the allergen and measuring the concomitant release of histamine or other pharmacological mediator. Since the IgE antagonist blocks IgE/$Fc_\epsilon RI$ interaction, a lower histamine concentration in the reaction mixture containing IgE antagonist indicates the presence of allergen-specific IgE in the patient's serum.

a. Construction of Genetically Engineered Cells

The method of the invention can be practiced with any genetically engineered mast cell or basophil host. Typically, a mast cell or bassphil host genetically engineered to express a $Fc_\epsilon RI$ α-chain native to the animal species of the patient is used in the method because $Fc_\epsilon RI$ α-chain derived from a given animal species will react with IgE derived from the same animal species. However, the invention also encompasses the use of an interspecies system wherein the $Fc_\epsilon RI$ a-chain expressed by the genetically engineered host cell is derived from a different animal species than that of the patient and is nevertheless capable of reacting with allergen-specific present in the patient's serum and effecting the release of pharmacological mediator or mediators upon allergen induction of sensitized host cells.

It will also be appreciated that the invention is not limited to the use of a $Fc_\epsilon RI$ α-chain with a particular degree of homology or heterology to the expression host cell. It is the ability of the host cell/$Fc_\epsilon RI$ α-chain system to effect IgE-mediated release of pharmacological mediator(s) upon allergen stimulus that is necessary for practicing the present invention. A genetically engineered mast cell or basophil suitable for use herein can be constructed by isolating mast cells or basophils from appropriate tissues in an animal, cloning the mast cells or basophils in tissue culture, isolating or synthesizing DNA encoding the $Fc_\epsilon RI$ α-chain of interest, cloning the $Fc_\epsilon RI$ α-chain-encoding DNA into an appropriate expression vector, transfecting the mast cell or basophil cell hosts with the recombinant expression vector, and detecting and isolating mast cell or basophil transfectants that express the recombinant $Fc_\epsilon RI$ α-chain on the cell surface and release pharmacological mediator or mediators in response to allergen cross-linking of patient IgE/$Fc_\epsilon RI$ α-chain complex.

1. Isolation of Mast Cells and Basophils

The invention can be practiced with mast cells harvested from any animal species, such as rodent, canine, feline, bovine, porcine, equine, ovine, and primate species, and the like. Candidate mast cell hosts can be obtained from a number of different types of animal tissues. Mast cells can be isolated from bone marrow, peritoneal cavity fluid, spleen, fetal liver, lymph nodes, or lung tissue harvested from an animal. Mast cells are then extracted from tissue samples and cloned by any competent method known in the art, e.g. the methods of Nabel et al., *Nature*, 291: 332–334 (1981) or Galli et al., *J. Cell Biol.*, 95: 435 (1982).

Suitable media for the culturing of cloned mast cells are known. Commercially available media include Dulbecco's Modified Eagle's medium (DMEM), Iscove's modified Dulbecco's modified medium media (IMDM) and others known. These preparations are advantageously supplemented or used with serum, e.g. heat inactivated fetal calf serum (FCS), and can include other sources of energy or nutrition and/or antibiotic or antiviral agents to prevent infection.

Preferably, the cloned mast cells are maintained in the presence of a growth/stimulation factor, of which several are known, including supernatant fluid taken from splenocytes stimulated with Con A, from cloned Lyl$^+$2$^-$ inducer T lymphocytes as described in Nagel et al., supra, or from WEHI-3 cells as described in Nagas et al., *Science*, 212: 333 (1981). Preferred is the mast cell growth factor obtained from cloned Lyl$^+$2$^-$ inducer T cells.

In a preferred embodiment, the candidate mast cell line is obtained as described in U.S. Pat. No. 4,559,310 to Cantor et al.

In another preferred embodiment, an immortal cell line, e.g. a neoplastic analog of the mast cell species of interest, is used as the mast cell host, such as the rat mast cell line RBL 2H3, and is grown in culture as described above.

The invention can be practiced with basophils harvested from any animal species, such as rodent, canine, feline, bovine, porcine, equine, ovine, and primate species, and the like. Candidate basophil cell hosts can be obtained from the blood of the animal. Leukocytes can be isolated from whole blood according to any of the procedures used for isolating naive donor leukocytes described in Section Ia above. Basophils can be separated from the rest of the leukocyte population by art-known procedures, such as reacting the leukocyte preparation with fluorochrome-labelled anti-Fc$_\epsilon$RI antibody or fluorochrome-labelled IgE followed by detection and segregation of the fluorescing cells with a flow-activated cell sorter. Alternatively, basophils can be isolated from the animal species of interest according to the method of Mulet al., *J. Immunol. Meth.*, 149: 207–214 (1992). The isolated basophils are then grown in suspension cell culture according to established methods, such as those described in Ishizaka et al., *J. Immunol.*, 134: 532–540 (1985).

2. Preparation of DNA Encoding Fc$_\epsilon$RI α-chain

DNA encoding the Fc$_\epsilon$RI α-chain of interest can be prepared by a variety of methods known in the art. If the DNA sequence is known, the DNA can be chemically synthesized according to the methods of Engels et al., *Agnew. Chem. Int. Ed. Engl.*, 28: 716–734 (1989), such as the triester, phosphite, phosphoramidite and H-phosphonate methods. Shimizu et al., *Proc. Natl. Acad. Sci. USA*, 85: 1907–1911 (1988) discloses a cDNA encoding the human Fc$_\epsilon$RI α-chain and a cDNA encoding the rat Fc$_\epsilon$RI α-chain. In addition to natural sequence DNAs, non-naturally occurring DNAs encoding the Fc$_\epsilon$RI α-chain of interest are suitable for use herein. In one embodiment, codons preferred by the expression host cell are used in the design of the Fc$_\epsilon$RI α-chain-encoding DNA.

Alternatively, DNA encoding the Fc$_\epsilon$RI α-chain of interest can be cloned from any cDNA library obtained from tissue believed to contain the Fc$_\epsilon$RI α-chain mRNA, generally mast cells or basophils harvested from the same animal species as the intended patient. The Fc$_\epsilon$RI α-chain gene can also be obtained from a genomic DNA library. Libraries are screened with probes designed to identify the gene of interest or the protein encoded by it. The entire cDNAs for the human and rat Fc$_\epsilon$RI α-chains are described in Shimizu et al. Nucleic acid encoding the Fc$_\epsilon$RI α-chains of other animal species is readily obtained by low stringency screening of genomic DNA, mast cell cDNA or basophil cDNA libraries of the species of interest using probes having oligonucleotide sequences from the Fc$_\epsilon$RI α-chain gene sequences of FIG. 2 on page 1909 of Shimizu et al. These probes usually will contain about 100 or more bases, and can consist of the entire rat or human Fc$_\epsilon$RI α-chain cDNA. The positive clones detected in the hybridization screening are then analyzed for homology to the human and rat Fc$_\epsilon$RI α-chains. In general, a candidate Fc$_\epsilon$RI α-chain from a given animal species will exhibit greater than about 30% amino acid sequence homology with the rat or human Fc$_\epsilon$RI α-chain and will have the immunoglobulin-like structure of the rat and human Fc$_\epsilon$RI α-chains as described by Shimizu et al.

Assays are conducted to confirm that the hybridizing full length genes encode the Fc$_\epsilon$RI α-chain of interest. The candidate Fc$_\epsilon$RI α-chain-encoding DNA is simply inserted into an expression vector and transfected into a host cell that ordinarily does not bind to IgE of the intended patient. Transfectants that acquire the ability to bind IgE of the intended patient thus bear the Fc$_\epsilon$RI α-chain gene of interest. For example, the candidate Fc$_\epsilon$RI α-chain-encoding DNA can be subcloned into the pSVL vector for expression by transfected COS-7 cells, the transfectants reacted with trinitrophenylated red blood cells and anti-dinitrophenyl (DNP) monoclonal IgE derived from the animal species of the intended patient, followed by detection of rosette formation as generally described in Miller et al., *Science*, 244: 334–336 (1989).

Since Shimizu et al. successfully used a full length rat Fc$_\epsilon$RI α-chain cDNA to detect and isolate a human Fc$_\epsilon$RI α-chain cDNA clone from a human mast cell cDNA library, it will be appreciated that either the rat or the human cDNA can be used to screen libraries for the genomic DNA or cDNA encoding Fc$_\epsilon$RI α-chain of other animal species with a high likelihood of success.

In another embodiment, polymerase chain reaction (PCR) methodology (U.S. Pat. No. 4,683,195; Erlich, ed., *PCR Tecnology*, 1989) to amplify the target DNA or RNA, e.g. as described in section 14 of Sambrook et al., *Molecular Cloning: A Laboratory Manual*, Cold Spring Harbor (1989). This method requires the use of oligonucleotide primers that will be expected to hybridize to the Fc$_\epsilon$RI α-chain-encoding nucleic acid of interest, and these readily are selected from the rat or human Fc$_\epsilon$RI α-chain-encoding cDNAs disclosed by Shimizu et al.

In yet another embodiment, the Fc$_\epsilon$RI α-chain protein is isolated from mast cells or basophils of the animal species of interest, the α-chain protein is partially or completely amino acid sequenced, the amino acid sequence information is used to design a pool of degenerate DNA probes, and the probe pool is synthesized and used to screen genomic DNA or cDNA libraries for the Fc$_\epsilon$RI α-chain gene of interest. This general procedure is described by Shimizu et al. for the cloning of the rat Fc$_\epsilon$RI α-chain-encoding cDNA.

3. Generation of Genetically Engineered Cells

After the Fc$_\epsilon$RI α-chain DNA is obtained, it is inserted into an vector that is capable of expressing the Fc$_\epsilon$RI α-chain DNA in the chosen mast cell or basophil cell host. The vector construct must contain a promoter sequence upstream of the Fc$_\epsilon$RI α-chain coding region (5' of the coding region on the sense strand) that is capable of effecting initiation of transcription of the Fc$_\epsilon$RI α-chain DNA by the RNA polymerase endogenous to the mast cell or basophil cell host. Optimally, the promoter sequence strongly promotes transcription of the Fc$_\epsilon$RI α-chain DNA. The expression vector can also contain enhancer and/or transcription termination sequences to facilitate transcription. Preferably, the host cells are transfected with an expression vector that contains a marker gene or are cotransfected with an expression vector and another vector containing a marker gene in order to facilitate detection or selection of transfectants. In a preferred embodiment, the VIS expression vectors described in Gilfillan et al., *J. Immunol.*, 149: 2445–2451 (1992) are used.

Following construction of a suitable expression vector, the mast cell or basophil cell host is transfected with the vector DNA by any method known in the art, such as calcium phosphate or DEAE-dextran precipitation, electroporation, viral transduction, or microparticle bombardment, and transfectants are detected or selected by growth in a selection medium.

The transfectant mast cells or basophils are then tested for surface expression of the $Fc_{\epsilon}RI$ α-chain of interest, e.g. using the method of Miller et al. described above or the methods described in Example 2 below. The candidate mast cell or basophil hosts that express the $Fc_{\epsilon}RI$ α-chain of interest are assayed for the ability to release pharmacological mediator(s), such as histamine, upon allergen-induced cross-linking of IgE/$Fc_{\epsilon}RI$ α-chain complex. The assay can be conducted by growing the candidate genetically engineered mast cells or basophils in medium as described in Section III(a)(1) above, contacting the cultured mast cells or basophils with serum containing a known allergen-specific IgE derived from the animal species of the intended patient as described in Example 2 below, contacting the sensitized mast cells or basophils with allergen as described in Example 2 below, and measuring the histamine release in the mixture by any of the methods described in Section I(e) above.

Preferably, a genetically engineered mast cell or basophil presensitized with allergen-specific IgE of the intended patient releases greater than 7%, and more preferably greater than 10%, of the total cellular histamine upon allergen challenge. The potential pool of genetically engineered mast cells and genetically engineered basophils with acceptable releasability is increased by incubating the genetically engineered cells in the presence of deuterium oxide ($D_2O$). As shown below in Example 2, the presence of $D_2O$ in the medium enhances allergen-induced histamine release. $D_2O$ can be effectively used at a final concentration in the incubation medium of about 10% to 100%, and preferably about 30% to 70%, and more preferably about 50% to 70%.

In a preferred embodiment, the rat mast cell line RBL48 described in Gilfillan et al. is used in the methods of the invention.

b. Preparation of Genetically Engineered Cells for Assay

The genetically engineered mast cells can be cultured for use in the methods of the invention by any convenient method known to be suitable for mast cell culture, such as the tissue culture methods used for mast cell cloning described in U.S. Pat. No. 4,559,310 to Cantor et al. After the genetically engineered cells are grown to confluence, they are trypsinized, suspended in culture medium, and diluted to a cell density of about $0.2\times10^6$ to $0.6\times10^6$ cells/ml, and preferably about $0.4\times10^6$ cells/ml. Next, the cells are seeded in the wells of microtitre plates at about 20,000 to 60,000 cells/well, and preferably about 40,000 cells/well, and cultured for about 1 day.

In a preferred embodiment, culture supernatants are removed, e.g., by aspiration, and the adherent cells remaining in the wells are washed one or more times with culture medium in order to reduce the presence of any histamine spontaneously released by the genetically engineered cells. Following the cell washes, the culture wells receive aliquots of fresh medium or, more preferably, a salt buffer designed to enhance release of pharmacological mediator(s) by the genetically engineered cells. Since the presence of $Ca^{2+}$ in the incubation medium has a substantial effect on histamine release (MacGlashan and Botana, supra), it is preferred that the buffer contains $Ca^{2+}$. Alternatively, the buffer can contain $Mg^{2+}$ to increase histamine release as described in Examples 1 and 2 below. In one embodiment, the buffer is a dilution of HBSS providing a final $Ca^{2+}$ concentration of about 0.13 mM to 0.65 mM, and preferably about 0.18 mM to 0.26 mM, and a final $Mg^{2+}$ concentration of about 0.09 mM to 0.45 mM, and preferably about 0.13 mM to 0.18 mM.

The genetically engineered basophils can be cultured for use in the methods of the invention by any convenient method known to be suitable for basophil suspension cell culture, such as the method of Ishizaka et al., supra. Preferably, the basophil suspension culture is diluted to a concentration of about 30,000 to 90,000 cells/ml, and preferably about 50,000 to 70,000 cells/ml. The dilution of the suspension culture can be performed with fresh culture medium or, more preferably, a salt buffer designed to enhance histamine release as described above.

In a preferred embodiment, the presence of spontaneously released histamine is reduced by separating the genetically engineered basophils from the culture medium, e.g. by centrifugation or filtration, and washing the cells one or more times with fresh culture medium. The washed cells are then resuspended in fresh culture medium or, more preferably, in a buffered salt solution suitable for promoting the release of pharmacological mediator(s) by the cells as described above. The cell suspension is adjusted to attain the desired cell concentration as described above.

In addition, the histamine releasing ability of the genetically engineered cells can be increased by including a suitable concentration of $D_2O$ (described in Section III(a)(3)above) in the suspension buffer or culture supernatant. In a preferred embodiment, the genetically engineered mast cells are cultured as described in Example 2 below.

c. Preparation of Patient Serum for Assay

Any fraction of a patient's blood which contains IgE and/or lacks $Fc_{\epsilon}RI^+$ immune cells is suitable for use in the diagnosis of allergy according to the present method. Since it is easily obtained, a patient serum sample is a convenient fraction for analysis.

d. Sensitization of Genetically Engineered Cells

The patient's serum is added to the genetically engineered cell preparation with or without IgE antagonist to form a blocked reaction mixture or a reaction mixture, respectively. IgE antagonist can be mixed with the genetically engineered cell preparation either prior to or at the same time that the patient serum is added to the mixture. Alternatively, the patient serum can be premixed with IgE antagonist and then mixed with the genetically engineered cell preparation. In embodiments using an adherent cell culture, the reaction mixture and the blocked reaction mixture can be formed by admixing patient serum with or without IgE antagonist to the culture supernatants. In embodiments using a suspension cell culture, the reaction mixture and the blocked reaction mixture can be formed by admixing patient serum with or without IgE antagonist to the cell suspensions.

In a preferred embodiment, heparin is present in the reaction mixtures at a concentration of about 1 to 10 U/ml, and preferably about 2 to 6 U/ml, and more preferably about 3 U/ml. The heparin component in the reaction mixtures is advantageously provided by obtaining or preparing the patient serum in a heparin buffer. Alternatively, a heparin component can be included in the cell culture medium or cell suspension buffer used in the reaction mixtures.

At least two mixtures of patient serum/genetically engineered cells are compared in parallel. In one mixture, IgE antagonist is used to block the binding of patient serum IgE to genetically engineered cells. In a second mixture, the patient serum is exposed to genetically engineered cells in the absence of IgE antagonist. In one embodiment, an IgE antagonist that binds to IgE is used in a range of concentrations in patient serum/genetically engineered cell mixtures to titer the allergen-specific IgE in the patient serum. The analysis of the effects of a range of IgE antagonist concentrations provides a powerful tool in assessing the severity of the patient's allergic condition. Optionally, serum samples known to contain allergen-specific IgE are also tested with or without IgE antagonist according to the present method in order to provide negative and positive controls, respectively.

The concentrations of patient serum and IgE antagonist used in the reaction mixtures will depend upon the $Fc_\epsilon RI$ $\alpha$-chain expression levels and cell concentrations of the particular genetically engineered cell used, the affinity of patient IgE for the $Fc_\epsilon RI$ $\alpha$-chain expressed by the host cell, and the affinity of the IgE antagonist for patient IgE and/or the $Fc_\epsilon RI$ $\alpha$-chain expressed by the host cell. Preferably, the IgE antagonist is present in sufficient concentration to reduce the interaction between genetically engineered cells and any patient IgE contained in the blocked reaction mixture. When total blockade of IgE/$Fc_\epsilon RI$ $\alpha$-chain interaction is desired, it is preferable to use an IgE antagonist concentration that is sufficient for saturation of the IgE and/or $Fc_\epsilon RI$ $\alpha$-chain present in the blocked reaction mixture. When anti-IgE monoclonal antibody is used as the IgE antagonist and a genetically engineered cell monolayer is contacted with patient serum at a final dilution of about 1:100 to about 1:2, and preferably about 1:10, a useful range of anti-IgE monoclonal antibody concentrations in the patient serum/genetically engineered cell mixture is about 0.5 to 100 µg/ml, and preferably about 1 to 10 µg/ml, and more preferably about 2 to 5 µg/ml. It will be appreciated that the optimum parameters for genetically engineered cell concentration, patient serum dilution, and IgE antagonist concentration in the reaction mixtures can be easily determined with routine experimentation for any embodiment of the present method.

The reaction mixture and blocked reaction mixture are incubated under conditions suitable for IgE binding to $Fc_\epsilon RI$ receptor. Preferred conditions consist of about 2 hours of incubation at approximately 37 C. in a humidified, 5% $CO_2$ incubator as described in Example 2 below.

e. Allergen Challenge of Sensitized Genetically Engineered Cells

Following incubation, the reaction mixture and the blocked reaction mixture are challenged with the allergen of interest. If attached cultures of genetically engineered cells are used, the culture supernatant is optionally removed, e.g. by aspiration, and replaced with a salt buffer solution with or without $D_2O$ (to maximize histamine release upon allergen challenge) as described in Section III(b) above. The allergen challenge is advantageously conducted in a reaction volume of approximately 50 to 200 1#and preferably about 100 to 150 µl. Thus, in the case of an adherent cell culture of sensitized cells, it is desirable to replace the culture supernatant with approximately 50 to 200 µl, and preferably about 100 to 150 µl, of the above described salt buffer. In the case of genetically engineered cell suspensions, it is desirable to use aliquots of approximately 50 to 200 µl, and preferably about 100 to 150 µl, of sensitized cell suspension to provide the reaction volumes for allergen challenge.

Allergen concentrations of about 0.01 µg/ml to 100 µg/ml, and more preferably about 0.05 µg/ml to 15 µg/ml, and still more preferably about 0.1 µg/ml to 1 µg/ml, are suitable for reacting most allergens with sensitized genetically engineered cells in the present assay.

The incubation conditions for the allergen reaction mixtures are chosen to allow the induction of histamine release. In a preferred embodiment, the reaction mixture is incubated for about 20 to 30 minutes at a temperature of at least 32° C., and more preferably at least 37° C.±1° C.

f. Assay of Histamine Release

The histamine release in the allergen reaction mixtures can be stopped by sharply lowering the temperature in the reaction vessels by any convenient method such as placing the microtiter plates on ice. For measurement of allergen-induced histamine release, reaction mixture supernatants are separated from cells by filtration or centrifugation, and the histamine in the supernatants can be determined by any of the histamine detection assay methods described in Section I(e) above. For measurement of total cellular histamine, the genetically engineered cells in the reaction mixtures are disrupted by any convenient method, e.g. sonication, Manton-Gaulin press, treatment with a detergent such as Triton X-100, or osmotic pressure and freeze thawing, the histamine is separated from cell debris by filtration or centrifugation, and the histamine is quantitated as described above.

Lastly, the percent inhibition of histamine release caused by the IgE antagonist is calculated. The allergen-induced histamine release can be expressed as a percent of total cellular histamine by dividing the allergen-induced histamine value by the total cellular histamine value for each of the blocked and unblocked reaction mixtures, yielding the blocked percentage and unblocked percentage, respectively. The percent inhibition caused by a particular concentration of IgE antagonist can be determined by subtracting the blocked percentage from the unblocked percentage, and dividing the difference by the unblocked percentage. Alternatively, the percent inhibition can be calculated by subtracting the amount of histamine released in the presence of IgE antagonist from the amount of histamine released in the absence of IgE antagonist, and dividing the difference by the amount of histamine released in the absence of IgE antagonist. The ability of the IgE antagonist to reduce histamine release indicates the presence of allergen-specific IgE in the patient's serum and thus identifies allergic reaction to the particular allergen. The amount of IgE antagonist needed to reduce histamine release is an indication of the clinical intensity and severity of allergic symptoms.

IV. Kit for Detection of Allergen-Specific IgE in Patient Serum with Genetically Engineered Cells The testing system of the present invention can be supplied in the form of a kit, the components of which comprise a vial containing a genetically engineered mast cell or genetically engineered basophil, a vial containing an IgE antagonist, and one or more vials containing allergen(s) of interest. The genetically engineered mast cell or basophil can be conveniently provided in frozen form, in which case revitalization by appropriate known thawing procedures is required before use. The kit can also include a vial containing a medium comprising essential nutrients, energy sources, growth factors, etc., capable of supporting the growth of the genetically engineered mast cell or basophil in cell culture and/or a vial containing a buffered salt solution suitable for promoting the release of pharmacological mediator(s) in the reaction mixtures as described in Section III(b) above.

Optionally, one or more vials containing IgE specific for the allergen(s) of interest are provided as a positive control. The positive control allergen-specific IgE is derived from the same animal species as the patient to be tested. The positive control allergen-specific IgE can be supplied in known concentrations to facilitate construction of a standard curve useful for titering the allergen-specific IgE in patient serum.

In one embodiment, the kit includes vials containing reagents used in the analysis of pharmacological mediator(s) released by the genetically engineered cells.

In another embodiment, the kit includes a package label or package insert providing instructions as to the use of the kit in any of the methods described in Section III above.

V. Screen of IgE Antagonists

The invention also provides a method for assaying the bioactivity of an agent for blocking IgE-induced immune cell sensitization. The method can be used for screening therapeutics for the treatment of allergic disease. The method can also be used to screen agents with IgE antagonist activity for use in the allergy diagnosis methods described above or for any other purpose. In general, the method involves the use of an agent to be tested in place of the IgE antagonist in the methods for diagnosing allergic disease described above. An agent is assayed for its ability to block the interaction between allergen-specific IgE and $Fc_\epsilon RI$ receptor by contacting the allergen-specific IgE with $Fc_\epsilon RI^+$ immune cells in the presence or absence of the agent. The allergen-specific IgE/$Fc_\epsilon RI$ interaction is assayed by adding allergen and measuring the concomitant release of histamine or other pharmacological mediator. A lower histamine concentration in the mixture containing the agent indicates the agent's IgE antagonist activity.

Any serum sample which contains IgE specific to an allergen of interest and lacks $Fc_\epsilon RI^+$ immune cells is suitable for use in the assay of an agent's activity in blocking IgE-induced immune cell sensitization. Appropriate serum samples can be obtained from allergic patients as described above. In this embodiment, an agent can be assayed for its ability to block allergen-specific IgE from a particular patient, providing a powerful tool for assessing the therapeutic efficacy of different agents in the particular patient. Commercially prepared plasma products are also suitable for use in the invention, such as the ragweed specific human plasmas (RSHP) used in the Examples below.

Fractions of naive donor blood or other naive donor tissue samples suitable for use in the assay of an agent's activity in blocking IgE-induced immune cell sensitization can be obtained and prepared as described in the methods for diagnosing allergic disease above.

The serum sample is added to the naive donor tissue sample with or without the agent to form a blocked sensitization mixture or a sensitized mixture, respectively. When whole blood or a blood fraction is used as the donor tissue, the serum and donor blood can be mixed in the proportions described in the methods for diagnosing allergic disease above.

At least two mixtures of serum/naive donor $Fc_\epsilon RI^+$ immune cells are compared in parallel. In one mixture, the agent is used to block the binding of serum IgE to naive donor $Fc_\epsilon RI^+$ immune cells. In a second mixture, the serum is exposed to naive donor $Fc_\epsilon RI^+$ immune cells in the absence of the agent to provide a positive control. In a preferred embodiment, a series of serum/donor tissue mixtures with a range of agent concentrations are used to assess the agent's efficacy in the treatment of allergic disease or to determine the agent's activity as an IgE antagonist. When the agent being tested is a monoclonal antibody and when the donor tissue being used is whole blood or a blood fraction, a useful range of antibody concentrations in the serum/blood donor mixture is preferably about 0.001 to 10 µg/ml, and more preferably about 0.01 to 5 µg/ml, and still more preferably about 0.01 to 2 µg/ml.

The agent can be mixed with the donor tissue either prior to or at the same time that the serum is added to the donor tissue mixture. Alternatively, the serum can be premixed with the agent and then added to the donor tissue mixture.

The donor tissue/serum mixtures are incubated under the conditions described in the methods for diagnosing allergic disease above.

Following incubation, aliquots of the sensitized mixtures and blocked sensitization mixtures are challenged with the allergen of interest. Suitable aliquot sizes, amounts of allergen, and incubation conditions for the allergen reaction mixtures are described in the methods for diagnosing allergic disease above.

The histamine released in the allergen reaction mixtures can be measured by any of the techniques described in the methods for diagnosing allergic disease above. Lastly, the percent inhibition of histamine release caused by the agent is calculated. The percent inhibition caused by a particular concentration of agent is determined by subtracting the amount of histamine released in the presence of the agent concentration from the amount of histamine released in the absence of the agent, and dividing the difference by the amount of histamine released in the absence of the agent. The ability of the agent to reduce histamine release is indicative of the agent's efficacy in the treatment of allergic disease and/or the agent's activity as an IgE antagonist. The amount of the agent needed to reduce histamine release is an indication of the agent's strength as an anti-allergy therapeutic and/or IgE antagonist.

In addition, the invention provides a method of screening agents for the ability to inhibit immune cell degranulation. In this method, immune cells from a patient treated with the agent or donor immune cells preincubated with the agent in vitro are first mixed with allergen-specific IgE in the presence or absence of IgE antagonist, and the mixtures are then challenged with the allergen. The ability of IgE antagonist to reduce histamine release would indicate the ability of the agent to inhibit immune cell degranulation. The method can be used to test an agent's ability to inhibit degranulation in both mast cells and basophils.

IgE antagonists suitable for use in the present invention include anti-IgE antibodies and fragments thereof, soluble $Fc_\epsilon RI$ receptor, IgE variants and fragments thereof, $Fc_\epsilon RI$ receptor-binding peptides, IgE-binding peptides, and any nonproteinaceous small molecule capable of disrupting or blocking the interaction between IgE and the $Fc_\epsilon RI$ receptor such that $Fc_\epsilon RI^+$ immune cells do not release pharmacological mediator or mediators in response to allergen stimulus. A compound can be screened for activity as an IgE antagonist according to the above-described methods for assaying the bioactivity of a agent in blocking IgE-induced immune cell sensitization.

The candidate antagonist is also screened for inability to induce immune cell histamine release. Such activity would impair the effectiveness of an IgE antagonist in the methods of the invention for diagnosing allergic disease. Moreover, the ability of an agent to trigger histamine release would be likely to stimulate or exacerbate allergies in patients and is therefore an undesirable characteristic for an anti-allergy therapeutic. The histamine release-inducing activity of an agent can be tested by mixing sensitized immune cells with the agent instead of allergen in the above-described methods for diagnosing allergic disease. Sensitized immune cells mixed with allergen or merely buffer serve as positive and negative controls, respectively. In a preferred embodiment, the agent is tested for induction of histamine release as described in the Examples below. If the agent fails to induce histamine release that is substantially above the level of the negative control, the agent is acceptable for use in the present invention.

VI Generation of IgE Antagonists

In a preferred embodiment, anti-IgE antibody is used as the IgE antagonist. The anti-IgE antibody can be any type of immunoglobulin, such as IgG, IgA, IgM, IgD, and IgE, including polyclonal and monoclonal forms of such antibodies raised against IgE.

Polyclonal antibodies to IgE generally are raised in animals by multiple subcutaneous (sc) or intraperitoneal (ip) injections of IgE and an adjuvant. It can be useful to conjugate IgE or a fragment containing the target amino acid sequence from the Fc region of IgE to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals ordinarily are immunized against the cells or immunogenic conjugates or derivatives by combining 1 mg or 1 µg of IgE with Freund's complete adjuvant and injecting the solution intradermally at multiple sites. One month later the animals are boosted with ⅕ to ¹⁄₁₀ the original amount of conjugate in Freund's incomplete adjuvant by subcutaneous injection at multiple sites. 7 to 14 days later animals are bled and the serum is assayed for anti-IgE titer. Animals are boosted until the titer plateaus. Preferably, the animal is boosted with the conjugate of the same IgE, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g. by fusion with myeloma cells or by Epstein-Barr (EB)-virus transformation and screening for clones expressing the desired antibody. The hybridoma technique described originally by Koehler and Milstein, *Eur. J. Immunol.*, 6: 511 (1976) and also described by Hammerling et al., In: *Monoclonal Antibodies and T-Cell Hybridomas*, Elsevier, N.Y., pp. 563–681 (1981) has been widely applied to produce hybrid cell lines that secrete high levels of monoclonal antibodies against many specific antigens.

The hybrid cell lines can be maintained in vitro in cell culture media. The cell lines producing the antibodies can be selected and/or maintained in a composition comprising the continuous cell line in hypoxanthine-aminopterin thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant by conventional methods such as precipitation, ion-exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are sterile filtered.

While routinely mouse monoclonal antibodies are used, the invention is not so limited; in fact, human antibodies can be used. Such antibodies can be obtained, for example, by using human hybridomas (Cote et al., *Monoclonal Antibodies and Cancer Theraphy*, Alan R. Liss, p. 77 (1985)). In fact, according to the invention, techniques developed for the production of chimeric antibodies (Cabilly et al., U.S. Pat. No. 4,816,567, Morrison et al., *Proc. Natl. Acad. Sci*, 81: 6851 (1984); Boulianne et al., *Nature*, 312: 643–646 (1984); Neuberger et al., *Nature*, 312: 604 (1984); Neuberger et al., *Nature*, 314: 268–270 (1985); Takeda et al., *Nature*, 314: 452 (1985); EP 184,187; EP 171,496; EP 173,494; PCT WO 86/01533; Shaw et al., *J Nat. Canc. Inst.*, 80: 1553–1559 (1988); Morrison, *Science*, 229: 1202–1207 (1985); Oi et al., *BioTechnques*, 4: 214 (1986)) by coupling an animal antigen-binding variable domain to a human constant domain can be used; such antibodies are within the scope of this invention. The term "chimeric" antibody is used herein to describe a polypeptide comprising at least the antigen binding portion of an antibody molecule linked to at least part of another protein (typically an immunoglobulin constant domain).

In one embodiment, such chimeric antibodies contain about one third rodent (or other non-human species) sequence and thus are capable of eliciting a significant anti-globulin response in humans. For example, in the case of the murine anti-CD3 antibody OKT3, much of the resulting anti-globulin response is directed against the variable region rather than the constant region (Jaffers et al., *Transplantation*, 41: 572–578 (1986)).

Humanized antibodies are used to reduce or eliminate any anti-globulin immune response in humans. In practice, humanized antibodies are typically human antibodies in which some amino acid residues from the complementarity determining regions (CDRs), the hypervariable regions in the variable domains which are directly involved with formation of the antigen-binding site, and possibly some amino acids from the framework regions (FRs), the regions of sequence that are somewhat conserved within the variable domains, are substituted by residues from analogous sites in rodent antibodies. The construction of humanized antibodies is described in Riechmann et al., *Nature*, 332: 323–327 (1988), Queen et al., *Proc. Natl. Acad. Sci. USA*, 86: 10029–10033 (1989), Co et al., *Proc. Natl. Acad. Sci. USA*, 88: 2869–2873 (1991), Gorman et al., *Proc. Natl. Acad. Sci.*, 88: 4181–4185 (1991), Daugherty et al., *Nucleic Acids Res.*, 19: 2471–2476 (1991), Brown et al., *Proc. Natl. Acad. Sci. USA*, 88: 2663–2667 (1991), Junghans et al., *Cancer Res.*, 50: 1495–1502 (1990), Fendly et al., *Cancer Res.*, 50: 1550–1558 (1990) and in PCT applications WO 89/06692 and WO 92/22653.

In some cases, substituting CDRs from rodent antibodies for the human CDRs in human frameworks is sufficient to transfer high antigen binding affinity (Jones et al., *Nature*, 321: 522–525 (1986); Verhoeyen et al., *Science*, 239: 1534–1536 (1988)) whereas in other cases it is necessary to additionally replace one (Riechmann et al., supra) or several (Queen et al., supra) FR residues. See also Co et al., supra.

The invention also encompasses the use of human antibodies produced in transgenic animals. In this system, DNA encoding the antibody of interest is isolated and stably incorporated into the germ line of an animal host. The antibody is produced by the animal and harvested from the animal's blood or other body fluid. Alternatively, a cell line that expresses the desired antibody can be isolated from the animal host and used to produce the antibody in vitro, and the antibody can be harvested from the cell culture by standard methods.

Particularly preferred for use in the methods of the invention is the humanized anti-IgE antibody E25 (rhuMAbE25) as described in the Examples below. The construction of rhuMAbE25 is disclosed in Presta et al., *J. Immunol.*, 151: 2623–2632 (1993).

Anti-IgE antibody fragments can also be used in the methods of the invention. Any fragment of an anti-IgE antibody capable of blocking or disrupting IgE interaction with immune cells or genetically engineered cells is suitable for use herein. Preferably, the antibody fragment is unable to trigger histamine release in immune cells or genetically engineered cells.

Suitable anti-IgE antibody fragments can be obtained by screening combinatorial variable domain libraries for DNA capable of expressing the desired antibody fragments. These techniques for creating recombinant DNA versions of the antigen-binding regions of antibody molecules (known as F(ab) fragments), which bypass the generation of monoclonal antibodies, are encompassed within the practice of this invention. One extracts antibody-specific messenger RNA molecules from immune system cells taken from an immunized animal, transcribes these into complementary DNA (cDNA), and clones the cDNA into a bacterial expression system. One example of such a technique suitable for the practice of this invention was developed by researchers at Scripps/Stratagene, and incorporates a proprietary bacteriophage lambda vector system that contains a leader sequence that causes the expressed F(ab) protein to migrate to the periplasmic space (between the bacterial cell membrane and the cell wall) or to be secreted. One can rapidly generate and screen great numbers of functional F(ab) fragments for those that bind the antigen. Such IgE-binding molecules (F(ab) fragments with specificity for the IgE protein) are specifically encompassed within the term "antibody" as it is defined, discussed, and claimed herein.

In a further embodiment of the invention, soluble $Fc_\epsilon RI$ receptor can be used as the IgE antagonist. Soluble $Fc_\epsilon RI$ receptors suitable for use herein include molecules comprising the IgE binding site in the extracellular domain (exodomain) of the $Fc_\epsilon RI$ $\alpha$ chain. The $\alpha$ chain of $Fc_\epsilon RI$ can be genetically modified such that the exodomain is secreted as a soluble protein in a recombinant expression system according to the method of Blank et al., *J. Biol. Chem.*, 266: 2639–2646 (1991) or Qu et al., *J. Exp. Med.*, 167: 1195. The candidate soluble $Fc_\epsilon RI$ receptor can be screened for activity as an IgE antagonist according to the above-described methods for assaying the bioactivity of a agent in blocking IgE-induced immune cell sensitization. Alternatively, the candidate soluble $Fc_\epsilon RI$ receptor can be screened for activity as an IgE antagonist by using the candidate soluble $Fc_\epsilon RI$ receptor to block the interaction between IgE and a genetically engineered cell in any of the methods for diagnosing allergy with genetically engineered cells described above.

The invention also encompasses the use of IgE-binding peptides in addition to anti-IgE antibodies and soluble $Fc_\epsilon RI$ receptor. Any IgE-binding peptide capable of disrupting or blocking the interaction between IgE and $Fc_\epsilon RI$ receptor is suitable for use herein. A candidate IgE-binding peptide can be screened for activity as an IgE antagonist according to the above-described methods for assaying the bioactivity of an agent in blocking IgE-induced immune cell sensitization. Alternatively, the candidate IgE-binding peptide can be screened for activity as an IgE antagonist by using the candidate IgE-binding peptide to block the interaction between IgE and a genetically engineered cell in any of the methods for diagnosing allergy with genetically engineered cells described above.

Preferably, the IgE-binding peptide is unable to induce histamine release in immune cells or genetically engineered cells. A candidate IgE-binding peptide can be tested by mixing sensitized immune cells (or sensitized genetically engineered cells) with the peptide instead of allergen in any of the above-described methods for diagnosing allergic disease. Sensitized cells mixed with allergen or merely buffer serve as positive and negative controls, respectively. If the candidate IgE-binding peptide fails to induce histamine release that is substantially above the level of the negative control, the peptide is acceptable for use in the methods of the invention.

In addition to IgE antagonists which interfere with IgE/$Fc_\epsilon RI$ receptor interaction by binding to IgE, such as anti-IgE antibodies, fragments thereof, soluble $Fc_\epsilon RI$ receptor and other IgE-binding peptides described above, the invention encompasses the use of IgE antagonists which disrupt IgE/$Fc_\epsilon RI$ receptor interaction by competing with IgE for binding to the $Fc_\epsilon RI$ receptor, thereby lowering the available $Fc_\epsilon RI$ receptor.

IgE variant is one example of a $Fc_\epsilon RI$ receptor-binding competitor that is suitable for use in the methods of the invention. IgE variants are forms of IgE possessing an alteration, such as an amino acid substitution or substitutions and/or an amino acid deletion or deletions, which reduces or eliminates the ability of the altered IgE molecule to sensitize immune cells and wherein the altered IgE molecule is capable of competing with IgE for binding to $Fc_\epsilon RI$ receptor. A candidate IgE variant can be screened for activity as an IgE antagonist according to the above-described methods for assaying the bioactivity of an agent in blocking IgE-induced immune cell sensitization. Alternatively, the candidate IgE variant can be screened for activity as an IgE antagonist by using the candidate IgE variant to block the interaction between IgE and a genetically engineered cell in any of the methods for diagnosing allergy with genetically engineered cells described above.

A candidate IgE variant can be tested for lack of immune cell-sensitizing activity or genetically engineered cell sensitizing activity by comparing the histamine release of IgE variant-sensitized cells and the histamine release of IgE-sensitized cells upon allergen challenge. If the level of histamine release in the mixture containing the candidate IgE variant is substantially lower than the level of histamine release in the mixture containing IgE, the variant is suitable for use in the methods of the invention.

Fragments of IgE variants are also suitable for use herein. Any fragment of an IgE variant capable of competing with IgE for binding to $Fc_\epsilon RI$ receptor can be used in the methods of the invention. A candidate IgE variant fragment can be tested for the desired activity according to the methods for screening candidate IgE variants described above.

The invention also encompasses the use of $Fc_\epsilon RI$ receptor-binding peptides in addition to IgE variants and fragments thereof. Any $Fc_\epsilon RI$ receptor-binding peptide capable of disrupting or blocking the interaction between IgE and $Fc_\epsilon RI$ receptor is suitable for use herein. A candidate $Fc_\epsilon RI$ receptor-binding peptide can be screened for activity as an IgE antagonist according to the above-described methods for assaying the bioactivity of an agent in blocking IgE-induced immune cell sensitization. Alternatively, the candidate $Fc_\epsilon RI$-binding peptide can be screened for activity as an IgE antagonist by using the candidate $Fc_\epsilon RI$-binding peptide to block the interaction between IgE and a genetically engineered cell in any of the methods for diagnosing allergy with genetically engineered cells described above.

Preferably, the $Fc_\epsilon RI$ receptor-binding peptide is unable to induce histamine release in immune cells or genetically engineered cells. A candidate $Fc_\epsilon RI$ receptor-binding peptide can be tested for lack of immune cell sensitizing activity (or genetically engineered cell sensitizing activity) by the same methods described above for testing the immune cell (or genetically engineered cell) sensitizing activity of IgE variants.

Practice of the invention is not limited to the use of peptide IgE antagonists. Any compound capable of functioning as an IgE antagonist is suitable for use in the methods of the invention, including non-proteinaceous small molecule compounds. Such a compound can be tested for IgE antagonist activity by use of the compound as the IgE antagonist in the methods described above. If the compound is unable to trigger the release of a pharmacological mediator or mediators in sensitized immune cells (or sensitized genetically engineered cells) and is capable of disrupting or blocking the interaction between IgE and the high affinity receptor $Fc_\epsilon RI$ on immune cells (or genetically engineered cells) such that the cells do not release a pharmacological mediator or mediators in response to allergen stimulus, the compound qualifies as an antagonist as defined, described and claimed herein.

Further details of the invention can be found in the following examples, which further define the scope of the invention. All references cited herein are expressly incorporated by reference in their entirety.

EXAMPLES

Example 1

1. MATERIALS AND METHODS a. Materials

Monoclonal antibodies produced by conventional hybridoma techniques were humanized and isolated as described by Carter et al., *Proc Natl Acad Sci USA:* 89: 4285–4289 (1992) and Presta et al., *J. Immunol,* 151: 2623–2632 (1993). These included murine anti-human IgE MAb (MAE1), which binds to IgE on basophils and triggers histamine release (Presta et al.), humanized anti-human IgE MAb (rhuMAbE25), humanized anti-HER2 MAb (rhuMAbHER2) and humanized anti-CD18 MAb (rhuMAbCD18). Human IgG Fc fragment was purchased from Organon Teknika Corp., West Chester, Pa. Ragweed antigens E-B & E-C (lot A-601-903A-185) were obtained from the National Institute of Health, Bethesda, Md. Dust mite allergen (*D. farinae* & *D. pteronyssinus* 50/50 mix, lot 6691UM) was from Miles Inc., West Haven, Conn. Ragweed specific human plasmas (RSMP) and dust mite specific human plasma (DMSHP) were obtained from North American Biological Company, Miami, Fla. Hank's balanced salt solution, (HBSS, 1x) was from Gibco BRL, Gaithersburg, Md. Bovine serum albumin (BSA, Fraction V) was obtained from Sigma, St. Louis, Mo. $CaCl_2.H_2O$ and $MgCl_2.6H_2O$ were analytical grade reagents obtained from Baker Chemical, Pittsburgh, N.J.

b. Blood Donors

Heparinized whole blood for the assays was obtained from a group of non-allergic or allergic individuals. The group consisted of seventeen women (non-pregnant) and twenty-six men with age ranging from 22 to 51 and a mean age of 34±7. Volunteers were not on medication and informed consent was obtained in all cases.

c. Ragweed Allergen-Induced Histamine Release Assay

Whole blood (5 mL) from prescreened donors was drawn into heparinized tubes (Becton Dickinson) and used in the assay within 4 hours. Blood was diluted 1:7 with HBSS/1% BSA. Nine parts of the diluted blood were added to one part of RSHP and incubated with or without rhuMAbE25 standards (final concentrations ranging from 0.01 to 2 µg/mL) for 2 hours at 37° C. in a humidified, 5% $CO_2$ incubator. After incubation, 100 1 aliquots of the samples were transferred to a round bottom 96-well non-tissue culture plate (Costar 3797) containing 50 1 buffer (HBSS/1% BSA provided by the enzyme immunoassay kit), ragweed allergen (0.3 µg/mL in PBS/0.01% BSA) or MAE1 (30 µg/mL in PBS/0.01% BSA) and further incubated for 30 min at 37° C. The incubation was stopped by transferring the plate to ice. Plates were centrifuged at 900×g for 5 min and the supernatants harvested for histamine determination. For each blood sample, total cellular histamine was determined by mixing 50 µl of the sample with 950 µl distilled water followed by two 15 minute cycles of freezing and thawing. Samples were centrifuged at 900×g for 5 minutes and the supernatants were collected. The concentration of histamine in the supernatant was determined by a histamine enzyme immunoassay kit (AMAC, Inc., Westbrook, Me.) following the instructions of the manufacturer. Briefly, histamine was acylated and allowed to compete with histamine acetylcholinesterase for binding to antibody coated onto microwells. After 18 hours, each well was rinsed and the bound enzymatic activity was measured by the addition of a chromogenic substrate (acetylthiocholine, dithionitrobenzoate). The intensity of the color developed at 405 nm was used to calculate the concentration of histamine in the sample with a standard curve obtained with standards furnished by the kit. The calculated concentration of histamine was then converted to percent of total cellular histamine. Using histamine release by ragweed as the denominator, the percent inhibition of ragweed-induced histamine release by rhuMAbE25 was calculated. The biological activity of various preparations of rhuMAbE25 was determined from the standard dilution curve in which percent inhibition of ragweed-induced histamine release was plotted against the concentration of rhuMAbE25 using a least square, non-linear 4 parameter fit program.

d. Divalant Cation Studies

The histamine release assay was performed in the same way as described in step c above except that the whole blood was diluted 1:7 in Hanks' balanced salt buffer without $Ca^{++}$ and $Mg^{++}$ (HBSS$^-$) containing added $CaCl_2.2H_2O$, $MgCl_2.6H_2O$, or $CaCl_2.2H_2O$ plus $MgCl_2.6H_2O$ at final concentrations of 0, 0.325, 0.625, 1.25, 2.5, 5 and 10 mM. After 2 hours of sensitization with 10% RSHP, the diluted blood was challenged with ragweed allergen (0.1 µg/mL) for 30 min at 37° C. The release of histamine in the supernatants was determined and converted to percent total cellular histamine.

e. Deuterium Oxide ($D_2O$) Studies

In screening blood donors for the assay, the effect of deuterium oxide was determined. Heparinized whole blood from seventeen non-allergic donors were sensitized with 10% RSHP as in the assay format described above and then challenged with ragweed allergen prepared in either PBS/0.01% BSA or deuterium oxide (final concentration of 33.3%). The release of histamine in the supernatants after 30 min incubation was quantitated and converted to percent total cellular histamine.

f. Dust Mite Allergen-Induced Histamine Release Assay

The whole blood of a non-allergic donor diluted 1:7 with Hanks buffer was separately preincubated for 2 hr, either in the presence or absence of rhuMAbE25 (1 µg/mL), with seven plasmas (final concentration of 10%) taken from subjects allergic to dust mite and then challenged with the dust mite allergen according to the procedure described in step c above. The concentration of histamine in the supernatant was quantitated.

2. RESULTS a. Inability of rhuMAbE25 to Trigger Histamine Release

A first study was performed to confirm that rhuMAbE25 does not bind to RSHP-sensitized basophils and trigger histamine release in the absence of antigen stimulation. Whole blood specimens from 12 donors were presensitized with 10% RSHP and challenged with 0.1 µg/mL of ragweed allergen, 10 µg/mL of MAE1 (a murine MAb which can bind to IgE on surface of basophils and trigger histamine release as described by Presta et al.), 10 µg/mL of rhuMAbE25, or HBSS/1% BSA. After incubation, the concentration of histamine in the supernatant was quantitated. Both ragweed allergen and MAE1 elicited histamine release. However, rhuMAbE25 did not induce histamine release above background levels (FIG. 1).

b. Sensitization of Basophils with RSHP

Figure 2:
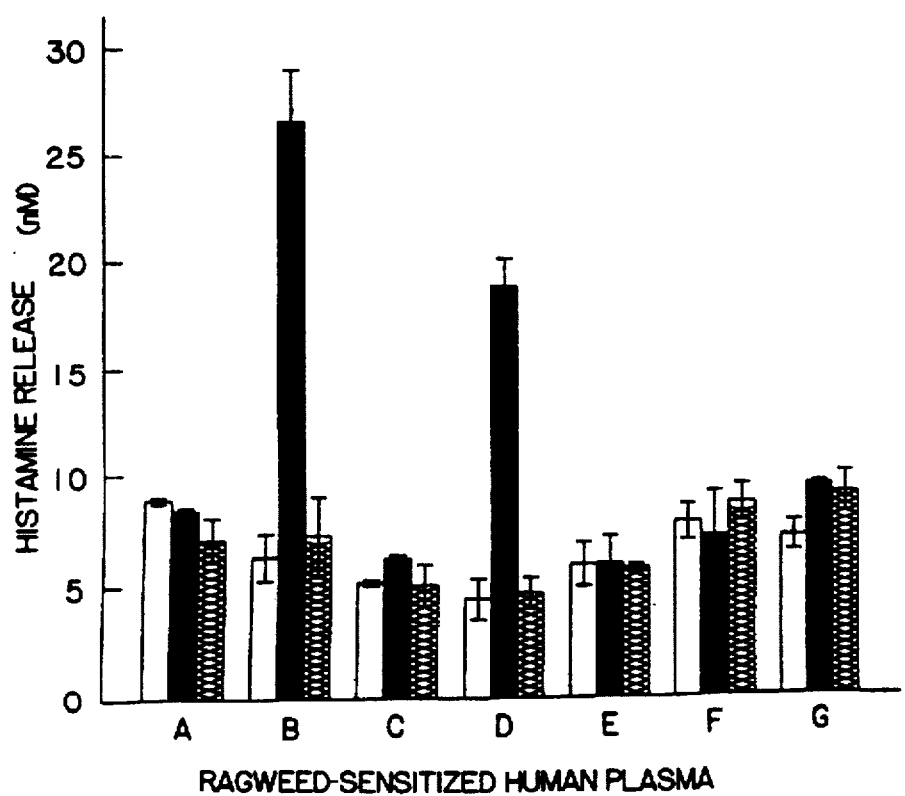
FIG. 2 is a graphic depiction of the screening of ragweed specific human plasmas. Whole blood from one naive donor was presensitized separately with 7 different human plasmas (A–G) taken from donors known to be allergic to ragweed in the absence (filled column) and presence (hatched column) of 1 µg/mL rhuMAbE25 prior to challenge of 0.1 µg/mL ragweed allergen. Mixtures presensitized with HBSS/1% BSA alone are represented with open columns. Each column represents the mean of duplicate determinations. Plasma B (lot 42-365054) was chosen to sensitize basophils in subsequent assays. Each error bar represents the range of duplicate determinations.
Figure 3:
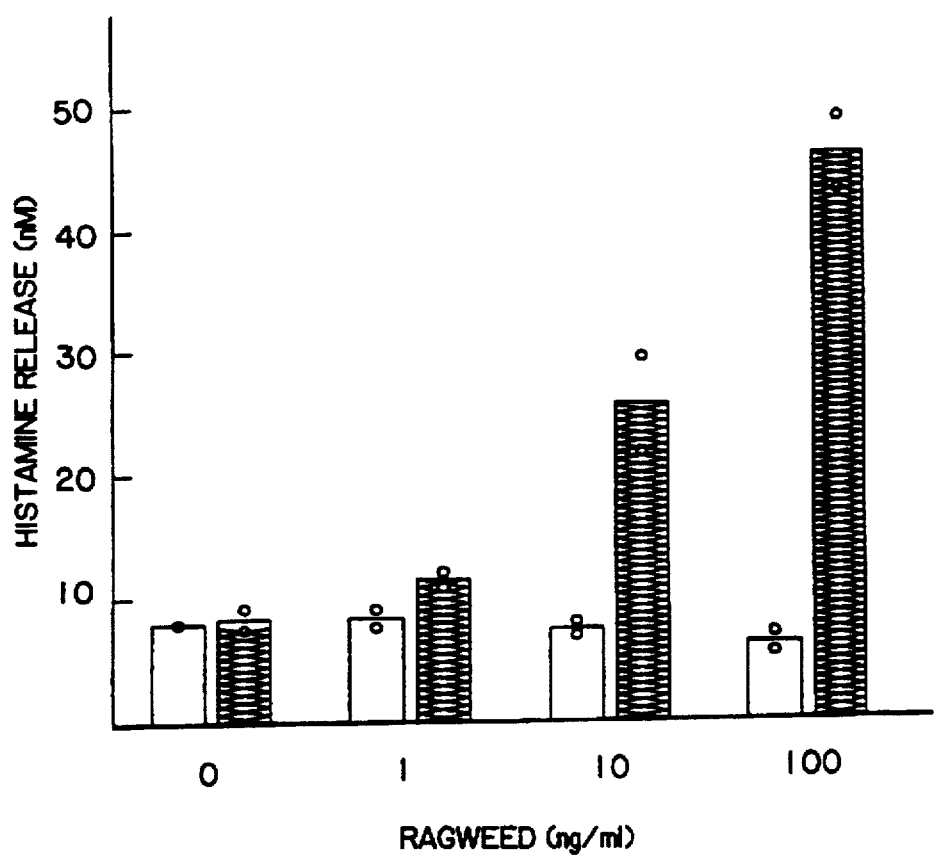
FIG. 3 is a graphic depiction of the effect that presensitization with 10% RSHP has on the ragweed-induced histamine release of whole blood. Heparinized blood specimens were preincubated for 2 hr at 37° C. with either PBS/0.1% BSA (open column) or 10% RSHP, lot 42-365054 (hatched column), prior to challenge with ragweed allergen at 0, 1, 10 and 100 ng/mL. The induced histamine release was quantitated and is expressed in terms of its concentration (nM) in the various reaction supernatants. Each column represents the range of duplicate determinations (open circle).

In order to maximally sensitize basophils, seven human plasma samples taken from individuals known to be allergic to ragweed were screened for their ability to induce histamine release. RSHP lot#42-365054 (total IgE 1.64 µg/mL) consistently resulted in the highest histamine release after challenge with ragweed allergen (FIG. 2). Consequently, RSHP (lot 42-365054) was used to sensitize the basophils in all subsequent assays. As shown in FIG. 3, presensitization of basophils in whole blood with exogenous human plasma containing IgE specific for ragweed (RSHP) was a prerequisite for subsequent histamine release upon challenge with ragweed allergen. In the absence of RSHP, only background levels of histamine were detected, while a dose-dependent release of histamine was observed in the presence of RSHP.

c. Donor Screens

Figure 4:
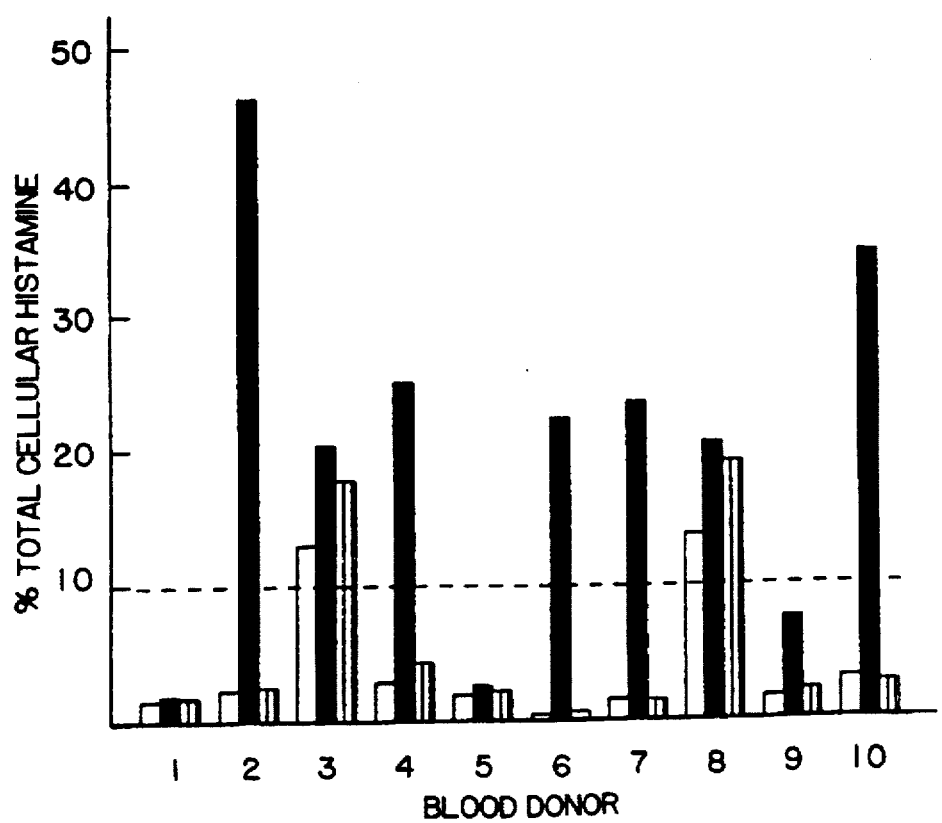
FIG. 4 is a graphic depiction of the histamine releasing ability of blood from different naive donors. Naive donor blood was screened for histamine releasing ability suitable for use in the bioactivity assay of rhuMAbE25. Donors' blood was sensitized by incubation with 10% RSHP in the absence (closed column) or the presence of 10 µg/mL rhuMAbE25 (hatched column) for 2 hours at 37° C. prior to challenge with 0.1 µg/mL ragweed allergen. Histamine release in response to HBSS/1% BSA challenge is represented by open columns. The induced histamine release is expressed as a percent of total cellular histamine. Each column represents the mean of duplicate determinations.

Non-allergic volunteers were prescreened prior to being used as donors for the assay. The screening protocol involved presensitizing donors' whole blood with 10% RSHP in the absence and presence of rhuMAbE25 (10 µg/mL) for 2 hours at 37° C. followed by challenge with ragweed allergen (0.1 µg/mL). Those donors with basophils that released greater than 10% of the total cellular histamine were selected for further study. As shown in FIG. 4, the cells from some donors did not release histamine upon ragweed challenge and conversely the cells from other donors were found to release histamine in the absence of allergen challenge. Of 43 volunteers, 12 were adequate 'responders' for routine use in this embodiment of the assay.

d. Kinetics of Histamine Release

Figure 5:
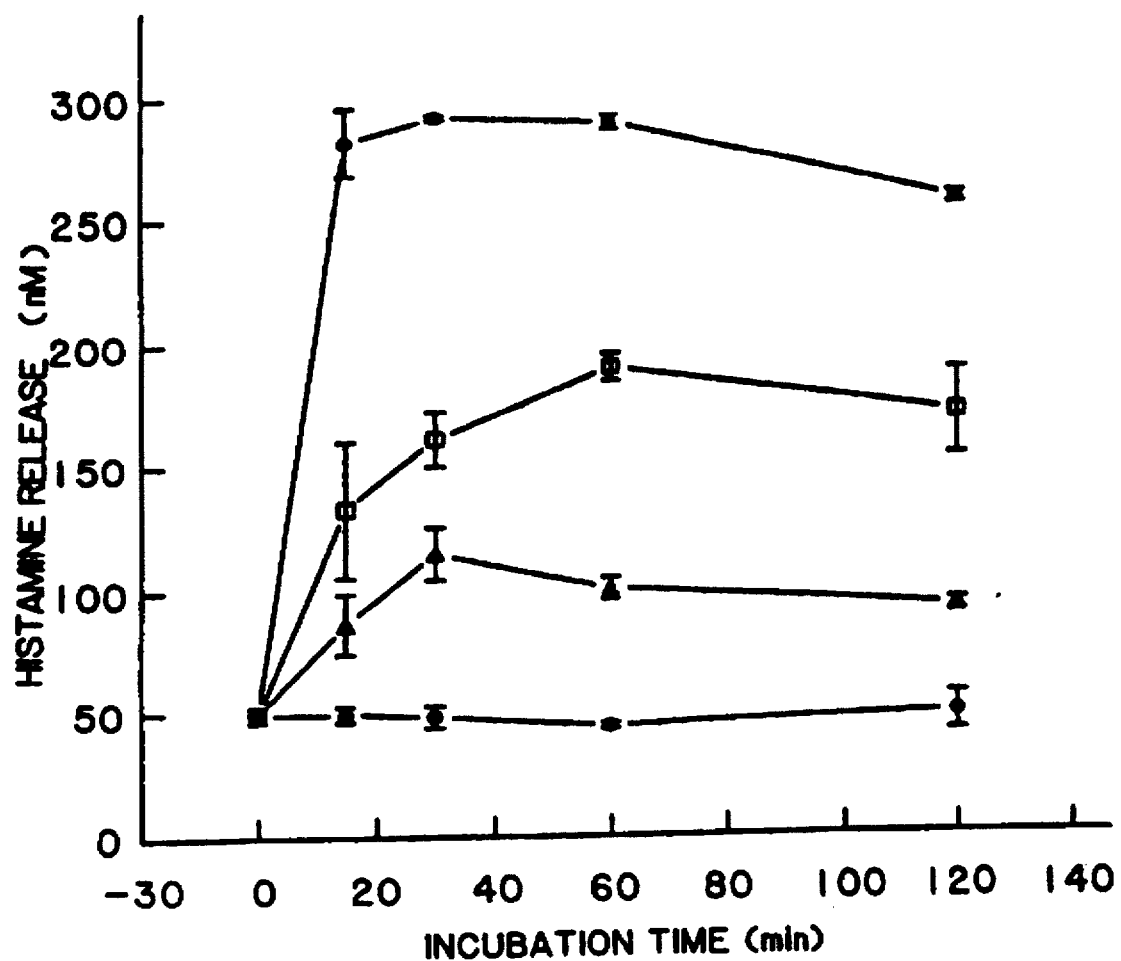
FIG. 5 is a graphic depiction of the kinetics of histamine release. Naive donors' blood presensitized with 10% RSHP in the presence of 0.5 µg/mL rhuMAbE25 (open square), 1 µg/mL rhuMAbE25 (open triangle), or no rhuMAbE25 (closed circle) was challenged 0.1 µg/mL ragweed allergen and incubated over a time course. Naive donors' blood presensitized with 10% RSHP and challenged with HBSS/1% BSA (open circle) was used as a negative control. The induced histamine release was quantitated and is expressed in terms of its concentration (nM) in the various reaction supernatants. The error bar represents the range of duplicate determinations.

The ragweed-induced histamine release from RSHP sensitized whole blood was rapid and reached a plateau after 20–30 min incubation (FIG. 5). Based on these results, a thirty minute incubation at about 37° C. was established as an optimal condition for the assay. The release of histamine was significantly reduced if the incubation was performed at ambient temperature.

e. Specificity

Preincubation of RSHP-sensitized whole blood with other humanized monoclonal antibodies, differing in complementary determining regions (CDR) but exhibiting an overall homology of about 95% to rhuMAbE25, produced no inhibitory effect on histamine release elicited by ragweed allergen as shown in Table I below. In addition, a human IgG Fc fragment had no inhibitory effect on ragweed-induced histamine release

TABLE I

| Treatment | % Total Cellular Histamine in Supernatant | |
|---|---|---|
| | − Ragweed Challenge | + Ragweed Challenge |
| Buffer | 0.7% | 53.6% |
| rhuMAbE25 | 0.6* | 1.8%** |
| rhuMAbHER2 | 0.5%* | 43.4%* |
| rhuMAbCD18 | 0.5%* | 59.9%* |
| huIgG Fc fragment | 0.5%* | 63.9%* |

*Concentration of antibody at 10 µg/mL
**Concentration of rhuMAbE25 at 1 µg/mL f. Variablity To determine interassay variability, a total of 23 assays were performed using blood from 12 donors. Results from these assays are tabulated in Table II below.

TABLE II

| | % Inhibition of Ragweed-Induced Histamine Release [rhuMAbE25] (µg/mL) | | |
|---|---|---|---|
| Experiment | 0.1 | 0.5 | 1 |
| 1 | 28.03 | 64.41 | 93.57 |
| 2 | 29.79 | 85.53 | 98.73 |
| 3 | 19.31 | 94.06 | 95.35 |
| 4 | 24.04 | 91.63 | 87.21 |
| 5 | 11.55 | 60.28 | 98.77 |
| 6 | 36.06 | 89.65 | 99.63 |
| 7 | 16.47 | 95.04 | 92.03 |
| 8 | 15.42 | 85.26 | 95.49 |
| 9 | 24.71 | 79.40 | 87.34 |
| 10 | 24.63 | 64.83 | 100.00 |
| 11 | 16.67 | 100.00 | 97.82 |
| 12 | 20.31 | 87.87 | 100.00 |
| 13 | 26.93 | 61.45 | 84.85 |
| 14 | 21.07 | 74.95 | 93.74 |
| 15 | 37.62 | 83.83 | 92.39 |
| 16 | 18.44 | 66.71 | 84.60 |
| 17 | 31.53 | 69.19 | 84.38 |
| 18 | 22.59 | 60.41 | 97.56 |
| 19 | 14.24 | 60.10 | 97.82 |
| 20 | 14.82 | 86.40 | 97.31 |
| 21 | 12.05 | 90.69 | 82.61 |
| 22 | 36.15 | 86.64 | 97.82 |
| 23 | 15.46 | 63.08 | 100.00 |

The percent inhibition of ragweed-induced histamine release by 0.1, 0.5 and 1 µg/mL rhuMAbE25 averaged 22.5%±7.8%, 78.3%±13.3% and 93.9±5.8% respectively. The interassay variation (% CV) calculated from the percent inhibition of histamine release by 0.5 µg/mL rhuMAbE25 was 17% (n=23). Variability within a donor over a time period of 8 weeks was less, averaging 9.05% (n=7).

g. Divalent Cations

Figure 6:
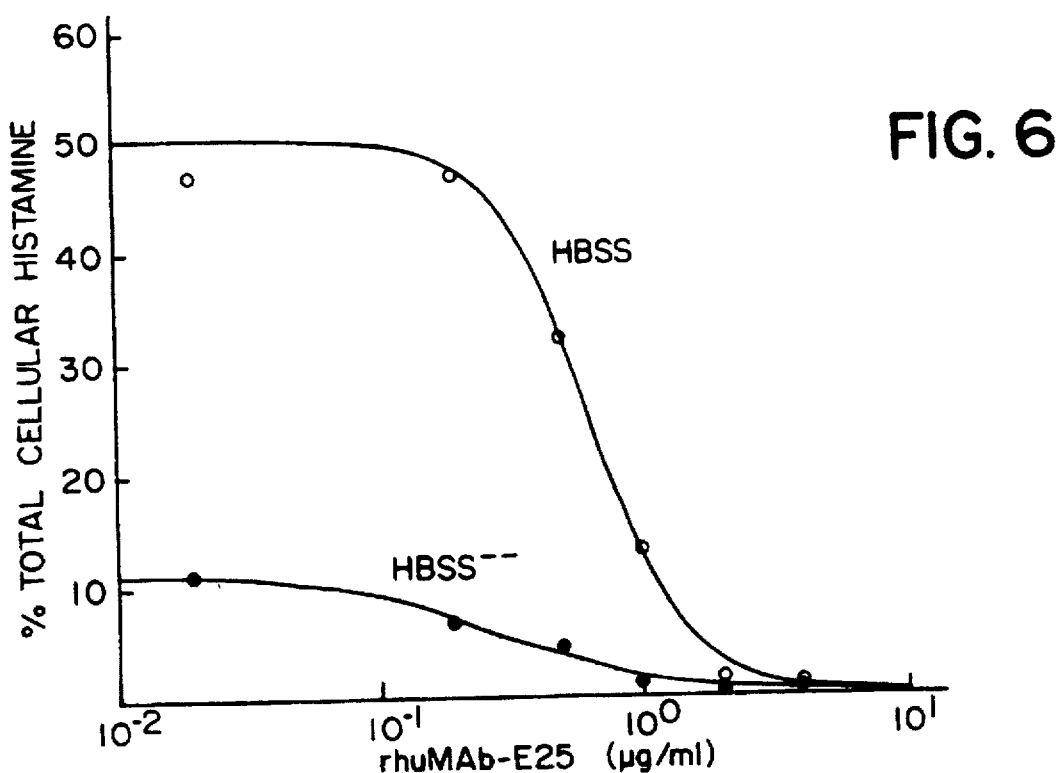
FIG. 6 is a graphic depiction of the decrease in histamine release caused by lack of $Ca^{+2}$ and $Mg^{2+}$ in the incubation medium. Heparinized whole blood from naive donors was diluted with either Hanks buffer (open circle) or Hanks buffer without $Ca^{+2}$ and $Mg^{2+}$ (HBSS$^-$) (filled circle) and incubated with various concentrations of rhuMAbE25 for 2 hr prior to challenge with ragweed allergen (0.1 µg/mL) for 30 minutes at 37° C. Each point represents the mean of duplicate determinations.
Figure 7:
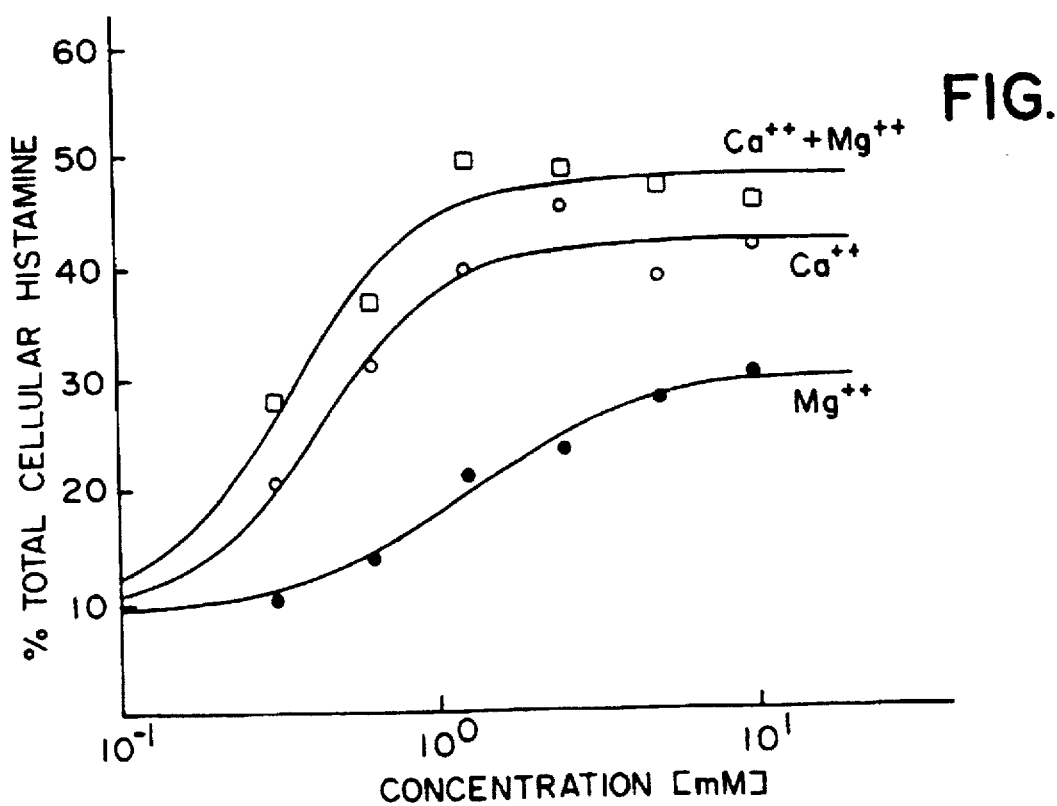
FIG. 7 is a graphic depiction of the effect of incubation medium $Ca^{2+}$ and Mg concentration on histamine release. Naive donor whole blood samples diluted with HBSS$^-$ containing various concentrations of $CaCl_2.2H_2O$ (open circle), $MgCl_2.6H_2O$ (filled circle), or $CaCl_2.2H_2O$ plus $MgCl_2.6H_2O$ (open square) were sensitized by 10% RSHP for 2 hr before challenge with ragweed allergen (0.1 µg/mL) for 30 minutes at 37° C. Release of histamine in the supernatant was quantitated and expressed as percent of total cellular histamine. Each point represents the mean of duplicate determinations.

It has been well established that histamine release is affected by $Ca^{2+}$ in the incubation medium (Lichenstein and Osler, *J. Exp. Med.*, 120: 507–530 (1964); Haydik and Ma, *Clin. Rev. Allergy*, 6: 141–162 (1988); MacGlashan and Botana, *J. Immunol*, 150: 980–991 (1993)). Consequently, the effects of $Ca^{2+}$ and $Mg^{2+}$ in the above-described assay were determined. When whole blood was diluted in Hanks balanced salt buffer depleted of $Ca^{2+}$ and $Mg^{2+}$ (HBSS$^{--}$) there was a substantial decrease of releasibility of histamine compared to whole blood diluted in Hanks balanced salt buffer containing $Ca^{2+}$ and $Mg^{2+}$ (FIG. 6). Adding equal concentrations of $CaCl_2.2H_2O$ and $MgCl_2.6H_2O$ to HBSS$^{--}$ restored histamine release. While adding back $MgCl_2.6H_2O$ alone partially restored release, the addition of $CaCl_2.2H_2O$ completely restored the releasability of histamine (FIG. 7).

h. Inhibition of Histamine Release by Preincubation with Blocking Antibodies

Figure 8:
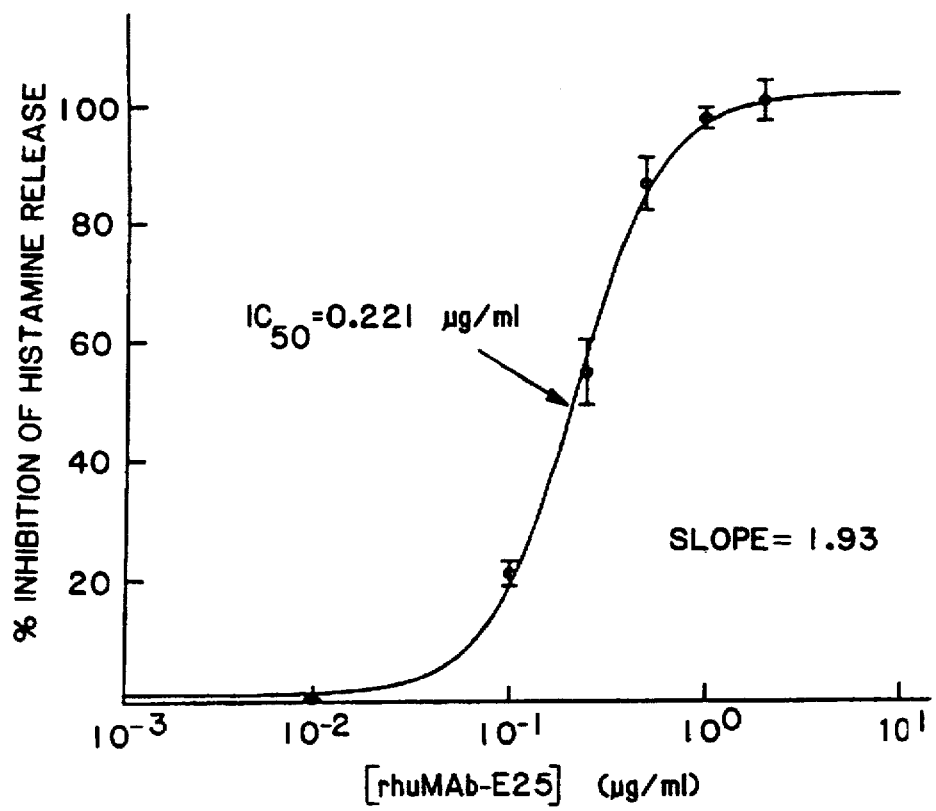
FIG. 8 is a graphic depiction of the effect of rhuMAbE25 concentration on ragweed-induced histamine release. Naive donors' blood was sensitized by incubation with 10% RSHP in the presence of various rhuMAbE25 concentrations for 2 hours at 37° C. prior to challenge with 0.1 µg/mL ragweed allergen for 30 minutes at 37° C. The induced histamine release was quantitated and is expressed in terms of its concentration (nM) in the various reaction supernatants. Each point represents the mean of duplicate determinations.
Figure 9:
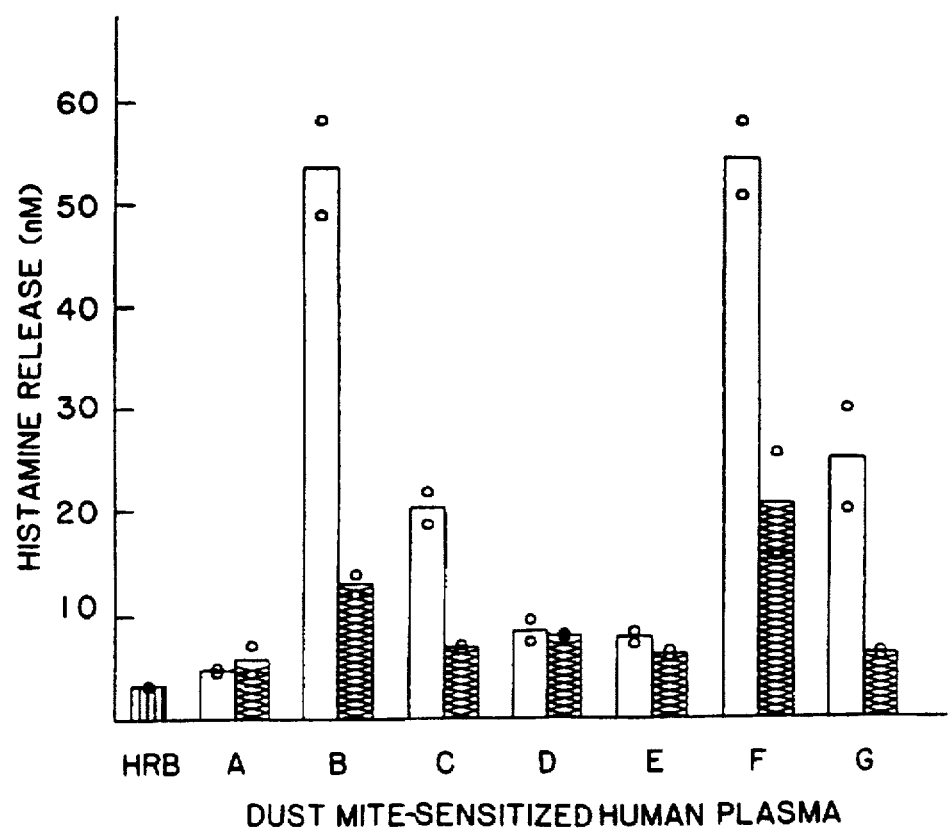
FIG. 9 is a graphic depiction of the effect of rhuMAbE25 on the histamine release of naive donor basophils elicited with plasma from subjects allergic to dust mite. Heparinized whole blood from one naive donor was diluted 1:7 in Hanks buffer and was separately preincubated in the presence (1 µg/ml) or absence of rhuMAbE25 for 2 hours with seven plasmas (A to G) taken from subjects allergic to dust mite and challenged with buffer (HBSS/1% BSA) and (0.1 µg/mL) dust mite allergen for 30 minutes at 37° C. The induced histamine release was quantitated and is expressed in terms of its concentration (nM) in the various reaction supernatants. Histamine release in the absence of rhuMAbE25 is depicted with open columns and histamine release in the presence of 1 µg/ml rhuMAbE25 is depicted with hatched columns. Each column represents the mean of two determinations (circle).

Preincubation of ragweed specific serum with either 0.5 or 1 µg/ml rhuMAbE25 substantially inhibited the release of histamine subsequently stimulated by ragweed challenge (FIG. 5). The inhibitory effects of rhuMAbE25 are best shown by plotting percent inhibition of ragweed-induced histamine release against the concentration of rhuMAbE25. A typical rhuMAbE25 standard curve is shown in FIG. 8. Inhibition of ragweed-induced histamine release was dose-dependent and can often be attained by rhuMAbE25 above 1 µg/ml. The optimal assay range for rhuMAbE25 was from about 0.1 to about 1 µg/ml with mean $IC_{50}$ of 0.255±0.079 µg/ml (n=15). The assay format can be readily modified to determine the effectiveness of rhuMAbE25 in blocking histamine release elicited by other allergens. An example is shown in FIG. 9. The whole blood of a non-allergic donor was separately sensitized, either in the absence or presence of rhuMAbE25 (1 µg/ml), with 10% plasma from subjects allergic to dust mite for 2 hr at 37° C. Next, the cells were challenged by the addition of dust mite allergen (100 ng/ml) for another 30 min. Histamine release in the supernatant was determined. It was observed that for patients B, C, F and G, the dust mite-induced histamine release was inhibited by 1 µg/ml of rhuMAbE25. Patient A, D and E did not significantly elevate histamine release above background after the challenge with dust mite allergen. A higher concentration of rhuMAbE25 was required to completely block dust mite-induced histamine release if 50%, as opposed to 10%, of the dust mite specific human plasma was used to sensitize the basophils. Thus, the assay format is useful in both demonstrating the presence of IgE specific for an allergen as well as the ability of an anti-IgE antibody to block the response elicited by an allergen.

i. Deuterium Oxide Studies

It has been reported that deuterium oxide enhances histamine release from leukocytes (Gillespie and Lichtenstein, J. Clin. Invest. 51: 2941–2947 (1972)). Therefore, the effect of deuterium oxide in the ragweed-induced histamine release was determined. $D_2O$ alone did not trigger histamine release. As shown in Table III below, incorporation of $D_2O$ in the incubation medium (final concentration of 33%) significantly enhances ragweed-induced histamine release. Out of seventeen randomly selected non-allergic donors, 15 donors (88%) exhibited histamine release greater than 20% of total cellular histamine upon challenge with ragweed allergen in this assay format. There was a mean increase of histamine release by 6.3 fold.

TABLE III

| Donor No. | % Total Cellular Histamine ||| 
|---|---|---|---|
| | Ragweed | Ragweed in $D_2O$ | No. of fold Increase |
| 13 | 9.3% | 37.8% | 4.1 |
| 14 | 3.1% | 30.3% | 9.8 |
| 15 | 13.0% | 25.11.9 | |
| 16 | 52.8% | 75.4% | 1.4 |

TABLE III-continued

| Donor No. | % Total Cellular Histamine |||
|---|---|---|---|
| | Ragweed | Ragweed in $D_2O$ | No. of fold Increase |
| 17 | 2.5% | 29.9% | 12.0 |
| 18 | 2.0% | 26.7% | 13.4 |
| 19 | 3.4% | 18.0% | 5.5 |
| 20 | 1.9% | 39.5% | 20.8 |
| 21 | 5.0% | 25.6% | 5.1 |
| 22 | 1.9% | 14.4% | 7.6 |
| 23 | 13.1% | 39.8% | 3.1 |
| 24 | 33.6% | 35.7% | 1.1 |
| 25 | 16.0% | 43.0% | 2.7 |
| 26 | 18.9% | 77.7% | 4.1 |
| 27 | 20.8% | 53.5% | 2.6 |
| 28 | 2.9% | 28.9% | 9.9 |
| 29 | 40.4% | 72.2% | 1.8 |
| mean | 14.2% | 39.6% | 6.3 |
| N | 17 | 17 | 17 |

Example 2

1. MATERIALS AND METHODS a. Materials

Monoclonal antibodies produced by conventional hybridoma techniques were humanized and isolated as described by Carter et al., Proc. Natl. Acad. Sci., 89: 4285–4289 (1992) and Presta et al., J. Immunol, 5: 2623–2632 (1993). These included humanized anti-human IgE MAb (rhuMAbE25)(referred to as "variant 12" in Presta et al.), humanized anti-HER2 MAb (rhuMAbHER2), humanized anti-CD18 MAb (rhuMAbCD18), and humanized anti-ICAM MAb (rhuMAbICAM). Goat anti-human IgE(ε) HRP conjugate was purchased from Kirkegaard & Perry Laboratories, Inc., Gaithersburg, Md. Recombinant human nerve growth factor (rhuNGF), tumor necrosis factor (rhuTNF), and interferon-gamma (rhuIFN-gamma) were generated, cloned and sequenced at Genentech (South San Francisco, Calif.). Ragweed antigens E-B & E-C (lot A-601-903A-185) were obtained from the National Institute of Health, Bethesda, Md. Standardized mite allergen (D. farinae) (cat. #6720UP, lot #E53L3533) and house dust mix allergen (cat. #4701ED, lot #C63J8308) were purchased from Miles Inc., Elkhart, Ind. Standardized cat pelt allergen (lot #3E00202) and Alternaria tenuis (lot #3J17242) allergen were obtained from Center Laboratories, Port Washington, N.Y. Human plasmas were obtained from North American Biological company, Miami, Fla. Hank's Balanced Salt Solution (HBSS, 1x) and glutamine were purchased from Gibco BRL, Gaithersburg, Md. Bovine serum albumin (BSA, Fraction V), o-phenylenediaminedihydrochloride (OPD) substrate and Triton X-100 were purchased from Sigma, St. Louis, Mo. Fetal bovine serum was purchased from Hyclone, Logan, Utah. Deuterium oxide ($D_2O$, 99.996% purity) was obtained from Aldrich Chem. Company, Milwaukee, Wis.

b. Blood donors

Heparinized whole blood was collected from a group of healthy, non-allergic or allergic individuals who were pre-screened prior to being used as donors for the human basophil histamine assay (HBHA). The screening protocol involved presensitizing donors' whole blood with 10% RSHP in the absence or presence of rhuMAbE25 (10 µg/mL) for 2 hours at 37° C. followed by challenge with ragweed allergen (0.1 µg/mL). Those donors with basophils that released greater than 10% of the total cellular histamine were selected for further study. No volunteers were on medication and informed consent was obtained in all cases.

c. Human Basophil Histamine Assay (HBHA)

Heparinized whole blood was diluted 1/7 with HBSS/1% BSA and mixed with 10% (v/v) allergen sensitized human plasma (e.g. ragweed specific human plasmas (RSHP). The mixture was incubated with or without rhuMAbE25 (prepared in PBS/0.01% BSA) for 2 hours at 37° C. in a humidified 5% $CO_2$ incubator. After incubation, samples were transferred to a 96-well plate (Costar #3797) containing either buffer (HBSS/1% BSA or 50% $D_2O$/0.8% NaCl/ 1.3 mM $CaCl_2$) or allergen (0.3 µg/mL in PBS/0.01% BSA or 50% $Dz_2O$/0.8% NaCl/1.3 mM $CaCl_2$) and further incubated for 30 minutes at 37° C. Plates were centrifuged at 900×g for 5 min at 4° C. and the supernatants were harvested for histamine determination. For each blood sample, total cellular histamine was determined by mixing 50 µL whole blood with 950 µL distilled water followed by two 15 min cycles of freezing and thawing. The concentration of histamine in the supernatant was determined with a histamine enzyme immunoassay kit (AMAC, Westbrook, Me.).

d. Cell culture

The RBL48 rat mast cell line was obtained as described by Gilfillan et al., supra. The RBL48 cell line was derived by transfecting parental rat mast cell line RBL2H3 with the human α-subunit of the high affinity IgE receptor $Fc_eRI$ (Gilfillan et al.). Cells were grown in sIMDM (iscove's modified Dulbecco's media supplemented with 10% fetal bovine serum, 2 mM glutamine, and 500 µg/mL of active geneticin (Gibco BRL #11811-031)) in a T175 tissue culture flask (Falcon #3028) at 37° C. in a humidified 5% $CO_2$ incubator. The cells were harvested by exposure to 4 mL of PBS/0.05% trypsin/0.53 mM EDTA (Gibco BRL #15400-013) for 2 min at 37° C. followed by centrifugation (400×g for 10 min) and resuspension in fresh sIMDM. The cells were optimally split at 1:5 ratio after confluence was attained.

e. Human plasma IgE binding ELISA assay

RBL48 cells, seeded at 40,000 cells per well, were cultured overnight at 37° C./5% $CO_2$ in a humidified incubator. After three washes with PBS/0.05% Tween 20 in a plate washer, the cells were fixed for 2 min with 200 per well of absolute alcohol at ambient temperature followed by six washes to remove residual alcohol. sIMDM containing 10% RSHP with or without rhuMAbE25 (10 µg/mL, final concentration) were incubated with cells for 1 hr at 37° C. After the incubation, cells were rinsed 6 times with PBS/ 0.05% Tween 20. The captured IgE were then reacted for 30 min at 37° C. with goat anti-human IgE-HRP followed by 30 min incubation with OPD substrate at ambient temperature. Reaction was stopped by the addition of 100 µL/well of 6N $H_2SO_4$. Absorbance at 492 nm was measured.

f. Rat Mast Cell Histamine Assay (RMCHA)

RBL48 cells were grown to confluence and then trypsinized as described in section d above. Cells in suspension were counted with a hemacytometer (Reichert-Jung Company, Buffalo, N.Y.) and the density was adjusted to $0.4\times10^6$ cells/mL. Cells were then seeded at 100 µL/well (40,000 cells per well) in a 96-well, U-shaped plate (Linbro #76-042-05) and cultured for 24 hr at 37° C. in a humidified 5% $CO_2$ incubator. After being washed once with 200 µL/well of sIMDM, the cells were preincubated for 2 hours with 100 µL/well of fresh sIMDM including 3 U/mL of sodium heparin (Becton Dickinson #367673) and 10% (v/v) of allergen sensitized human plasma containing allergen specific IgE either in the presence or absence of rhuMAbE25 standards (final concentrations ranging from 0.078 to 10 µg/mL) at 37° C. After incubation, culture medium in the well was removed by aspiration and adherent cells were washed 3 times with sIMDM. The cells were then incubated with 100 µL/well of histamine release buffer (HRB) (50% $D_2O$/0.8% NaCl/1.3 mM $CaCl_2$/sIMDM), allergen (0.1 µg/mL in HRB), or 0.5% triton solution (for total histamine release) for 30 min at 37° C. Plates were centrifuged at 900×g for 5 min at 4° C. and the supernatants were harvested and diluted 1000 times in PBS for total histamine release and 80 times for allergen-induced histamine release. The concentration of histamine in the supernatant was determined as described for the HBHA assay in section c above.

g. Correlation study of RMCHA and HBHA 15 samples of rhuMAbE25 (stored at -70° C., 2°-8° C., 25° C., and 40° C. for 1 to 18 months) were tested in parallel for the ability to inhibit ragweed-induced histamine release in both the HBHA and the RMCHA. Two concentrations (0.625 and 1.25 µg/mL for RMCHA, 0.25 and 0.5 µg/mL for HBHA) of each sample were used in the assays as described in sections c and f above. Protein concentrations of samples were determined from the rhuMAbE25 standard curve. The recovered concentrations (after correction for the dilution factor) of samples were calculated.

In a separate study, a panel of 5 allergens (prepared in 50% glycerin) that included mite (*D. farinae*), house dust mix, ragweed, cat pelt, and *Alternaria tenuis* was used to screen a panel of 8 human plasmas (7 allergic individual plasma samples from North American Biological company, Miami, Fla. and 1 pooled plasma sample from Genentech Inc., South S.F., Calif.) in both the RMCHA and the HBHA. The RBL48 rat mast cells and the naive donor blood basophils were first sensitized for 2 hr at 37° C. with 10% (v/v) human plasma in the presence or absence of rhuM-AbE25 (1 µg/mL, prepared in sIMDM/3 U/mL sodium heparin for RMCHA and in PBS/0.01% BSA for HBHA), then challenged with buffer (for HBHA, 33% D2O/0.8% NaCl/1.3 mM $CaCl_2$, for RMCHA, 33% $D_2O$/0.8% NaCl/ 1.3 mM $CaCl_2$/sIMDM) or a single dose of allergen (at final concentration of 0.1 µg/mL, assuming 333.3 AU/mL=33.33 BAU/mL=100 PNU/mL=1 µg/mL) in buffer with 33% $D_2O$. Histamine concentration in the supernatant was determined as described above.

h. Data Analysis

Histamine concentration was determined from the histamine standard curve using the "Read" computer program. Percent inhibition was calculated by MicroSoft Excel 4.0 program. Graphs were drawn using the KaleidaGraph 3.0 program. Statistics were analyzed in StatView 4.0 program.

2. Results a. Binding of IgE to RBL48 cells

Figure 10:
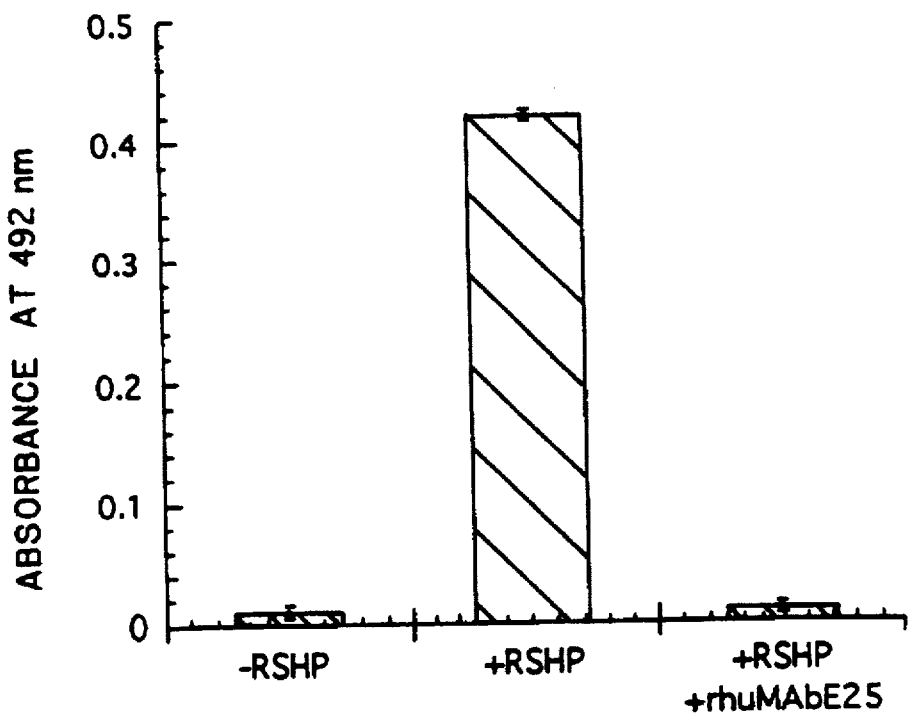
FIG. 10 is a graph depicting the inhibition of human IgE binding to RBL48 cells by rhuMAbE25. RBL48 cells were seeded at 40,000 cells/well and cultured overnight at 37° C. in a 5% $CO_2$ incubator prior to alcohol fixation. Fixed cells were incubated at 37° C. for one hour in one of the following media: (1) Iscove's modified Dulbecco's medium supplemented with 10% fetal bovine serum, 2 mM glutamine, and 500 µg/ml of active geneticin (sIMDM)(Gibco BRL#11811-031); (2) sIMDM/10% RHSP; or (3) sIMDM/10% RHSP/10 µg/ml rhuMAbE25. Following incubation, cells were rinsed 6 times with PBS/0.05% Tween 20, and then reacted for 30 minutes at 37° C. with horse radish peroxidase (HRP)-conjugated goat anti-human IgE (1/10;000 dilution) followed by 30 minutes of incubation with o-phenylenediaminedihydrochloride (OPD) substrate at ambient temperature. Each bar represents the mean of duplicate determinations.

The binding of IgE to RBL48 cells was evaluated in an IgE binding ELISA which uses an alcohol-fixed RBL48 monolayer to determine whether human IgE in the RSHP (total IgE measured at 1.64 µg/mL) could bind to the α-subunit of the $Fc_eRI$ receptors expressed on the surface of the RBL48 cells. FIG. 10 demonstrates that the IgE present in the RSHP does indeed bind to the $Fc_eRI$ receptors of the RBL48 cells. In addition, this binding is specific to IgE since the addition of a blocking anti-IgE monoclonal antibody, rhuMAbE25, completely abolishes the binding.

b. Specificity of the RMCHA

A RMCHA was performed (Table IV) to demonstrate that rhuMAbE25, like other recombinant human monoclonal antibodies such as anti-HER2, anti-CD18, and anti-ICAM and recombinant human cytokines such as IFN-γ, TNF, and NGF, when applied alone to the RBL48 cells, failed to induce mast cell degranulation. RBL48 cells were seeded at 40,000 cells/well and were cultured overnight at 37° C. in a 5% $CO_2$ incubator. Cells were preincubated for 2 hours with either sIMDM/50% $D_2O$, rhuMAbE25 (10 µg/mL), rhuM-AbHER2 (10 µg/mL), rhuMAbCD18 (10 µg/mL), rhuM-AbICAM (10 µg/mL), rhuIFN-γ(10 µg/mL), rhuTNF (10 µg/mL), or rhuNGF (10 µg/mL) in the presence of 10% (v/v) RSHP at 37° C. After three washes with sIMDM, cells were challenged with 0.1 µg/mL of ragweed allergen in the presence of 50% $D_2O$ for 30 min at 37° C. In addition, RSHP-sensitized cells were directly challenged with either rhuMAbE25 (10 µg/mL), rhuMAbHER2 (10 µg/mL), rhuM-AbCD18 (10 µg/mL), rhuMAbICAM (10 µg/mL), rhuIFN-γ (10 µg/mL), rhuTNF (10 µg/mL), or rhuNGF (10 µg/mL) alone for 30 min at 37° C. Each of the values shown in Table IV below represents the mean of triplicate determinations.

TABLE IV

Specificity of RMCHA for rhuMAbE25

| Treatment supernatant | % Total cellular histamine in | |
|---|---|---|
| | − Ragweed challenge | + Ragweed challenge |
| Buffer | 2.0 ± 0.2 | 22.0 ± 0.1 |
| rhuMAbE25 | 2.7 ± 0.5 | 2.1 ± 0 |
| rhuMAbHER2 | 2.0 ± 0.3 | 23.6 ± 0.1 |
| rhuMAbCD18 | 2.3 ± 1.2 | 22.9 ± 0.7 |
| rhuMAbICAM | 1.7 ± 0 | 23.7 ± 1.4 |
| rhuIFN-γ | 2.3 ± 0.9 | 23.3 ± 1.1 |
| rhuTNF | 1.6 ± 0.1 | 23.9 ± 0.2 |
| rhuNGF | 2.0 ± 0.5 | 22.9 ± 0.7 |

No inhibition of histamine release was observed when samples were preincubated with 10 µg/mL of the aforementioned antibodies and cytokines. Moreover, preincubation of ragweed specific human plasma with 10 µg/mL of rhuM-AbE25 completely abolished histamine release induced by 0.1 µg/mL of ragweed in the presence of 50% D2O.

c. Effect of temperature and calcium

Figure 11:
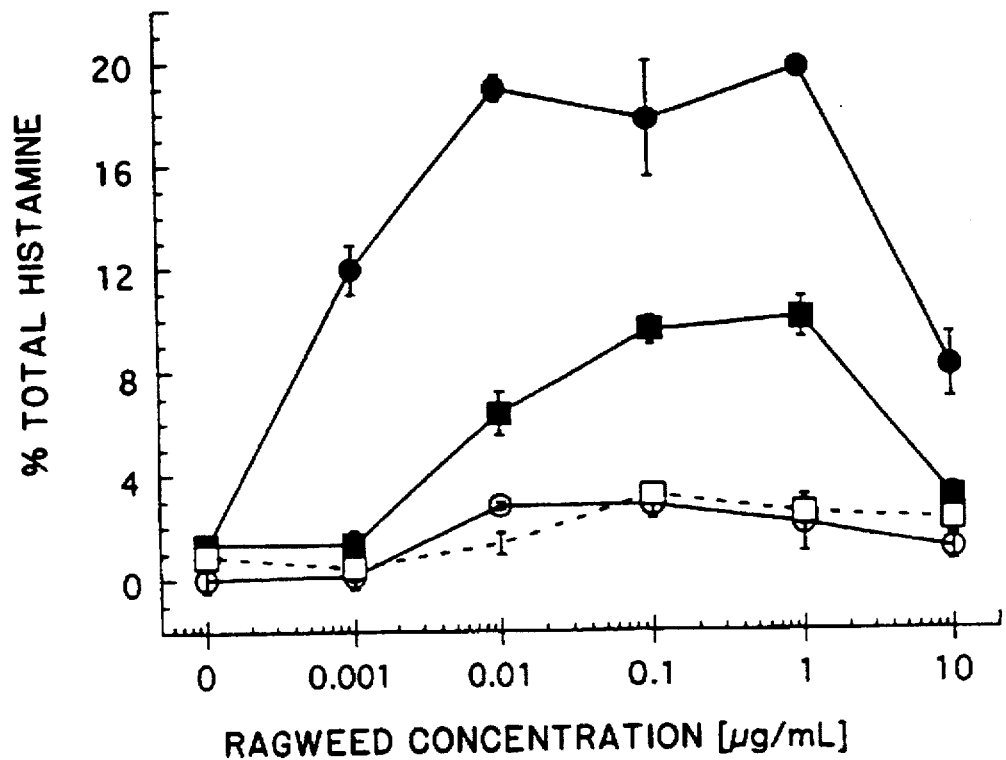
FIG. 11 is a graph depicting the effect of temperature and $Ca^{2+}$ concentration on ragweed-induced histamine release in RBL48 cells. RBL48 cells were seeded at 40,000 cells/well and cultured overnight at 37° C. in a 5% $CO_2$ incubator. Cells were preincubated at 37° C. for 2 hours with sIMDM containing 10% (v/v) RSHP and then challenged with 0 µg/ml, 0.001 µg/ml, 0.01 µg/ml, 0.1 µg/ml, 1 µg/ml, or 10 µg/ml ragweed allergen in 50% $D_2O$ at room temperature (open circle), in 50% $D_2O$ at 37° C. (filled circle), in sIMDM at 37° C. (filled square), or in 50% D2O/2.5 mM EDTA at 37° C. (open square). Each point represents the mean of duplicate determinations.

Histamine release induced by ragweed in the RMCHA was dependent on the concentration of ragweed, temperature, and calcium ions (FIG. 11). When the ragweed challenge step was incubated in the presence or absence of 50% $D_2O$ at 37° C., a bell-shaped dose-dependent histamine release curve that reaches maximal release at 0.1 µg/mL was observed. The release of histamine elicited by ragweed was attenuated or abolished if the incubation was performed either in the presence of 2.5 mM EDTA or at ambient temperature.

d. Time course of histamine release

Figure 12:
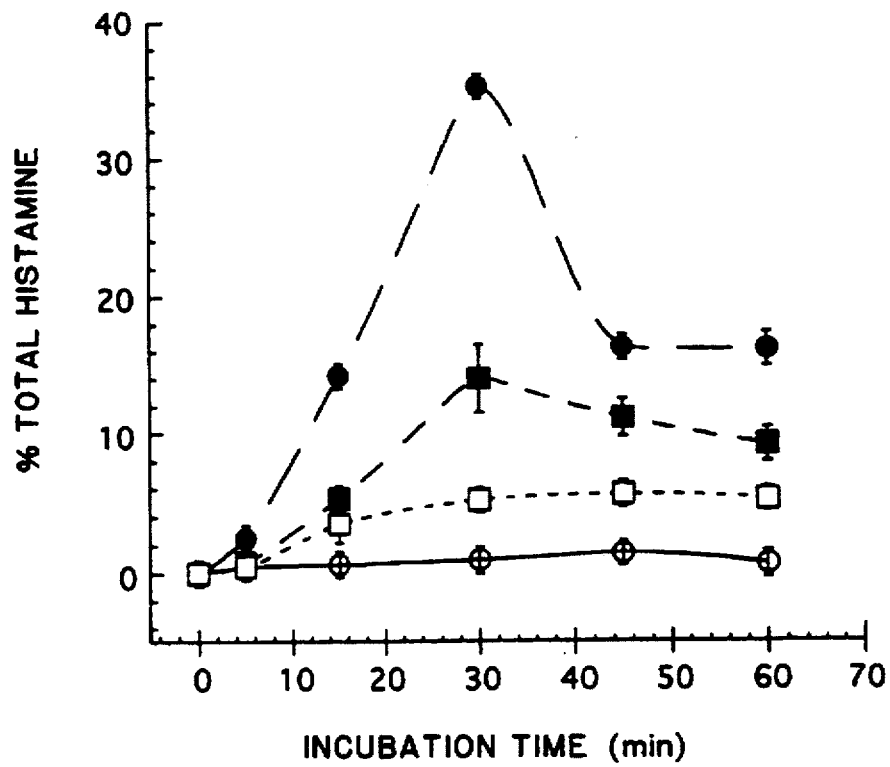
FIG. 12 is a graph depicting a time course of ragweed-induced histamine release by RBL48 cells in the presence of 50% $D_2O$. RBL48 cells were seeded at 40,000 cells/well and cultured overnight at 37° C. in a 5% $CO_2$ incubator. Cells were preincubated for 2 hours with sIMDM or sIMDM/10 µg/ml rhuMAbE25 in the presence of 10% (v/v) RSHP at 37° C. After 3 washes with sIMDM, cells were challenged with one of the following mixtures: (1) histamine release buffer (HRB) (50% $D_2O$, 0.8% NaCl, 1.3 mM $CaCl_2$, sIMDM)(open circle); (2) HRB and 0.1 µg/ml of ragweed allergen (filled circle); (3) HRB, 0.1 µg/ml of ragweed allergen, and 0.5 µg/ml rhuMAbE25 (filled square); or (4) HRB, 0.1 µg/ml of ragweed allergen, and 1 µg/ml rhuMAbE25 (open square). Each point represents the mean of duplicate determinations.
Figure 13:
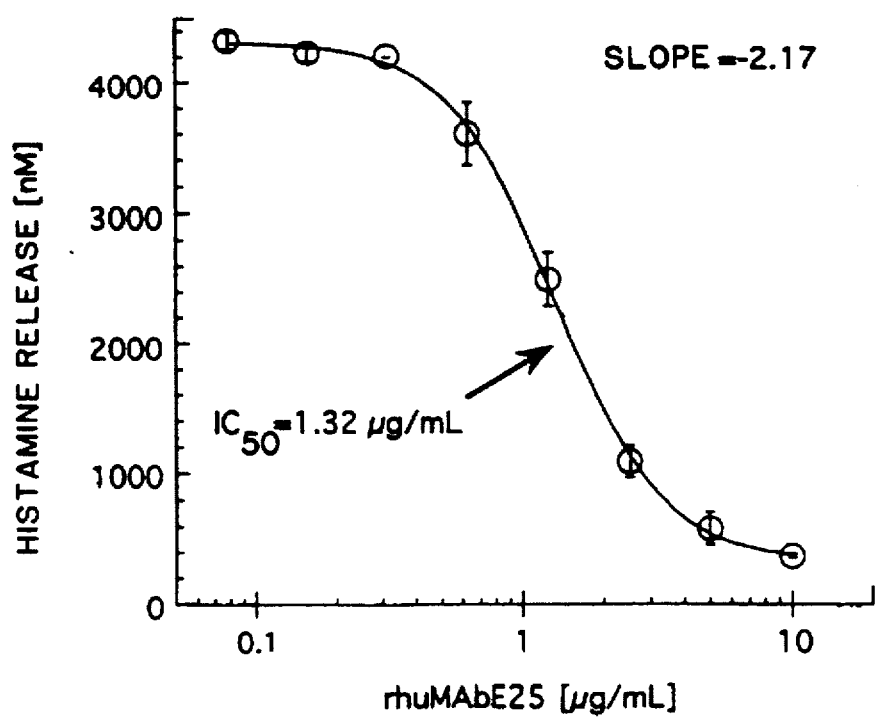
FIG. 13 is a graph depicting rhuMAbE25 inhibition of ragweed-induced histamine release in RBL48 cells. RBL48 cells were seeded at 40,000 cells/well and cultured overnight at 37° C. in a 5% $CO_2$ incubator. Cells were preincubated for 2 hours with rhuMAbE25 at 0.078, 0.156, 0.313, 0.625, 1.25, 2.5, 5 and 10 µg/ml concentrations in the presence of 10% (v/v) RSHP at 37° C. After 3 washes with sIMDM, cells were challenged with HRB, 0.1 µg/ml ragweed allergen, 50% $D_2O$ for 30 minutes at 37° C. Each point represents the mean of duplicate determinations.

The data presented in FIG. 12 demonstrates that ragweed-induced histamine release at 37° C. is time-dependent and reaches maximal release at 30 min incubation. When the incubation time was increased to 45 min or 60 min, the concentration of histamine in the supernatant dropped sharply from 36% to 16% of total cellular histamine. In addition, preincubation of ragweed specific plasma with either 0.5 or 1 µg/mL of rhuMAbE25 inhibited the release of histamine induced by ragweed allergen. A typical standard curve for quantitating the biological activity of rhuMAbE25 is shown in FIG. 13. Inhibition of ragweed-induced histamine release by rhuMAbE25 has a mean $IC_{50}$ of 1.19±0.31 µg/mL (n=25).

e. Correlation of RMCHA with HBHA

Figure 14:
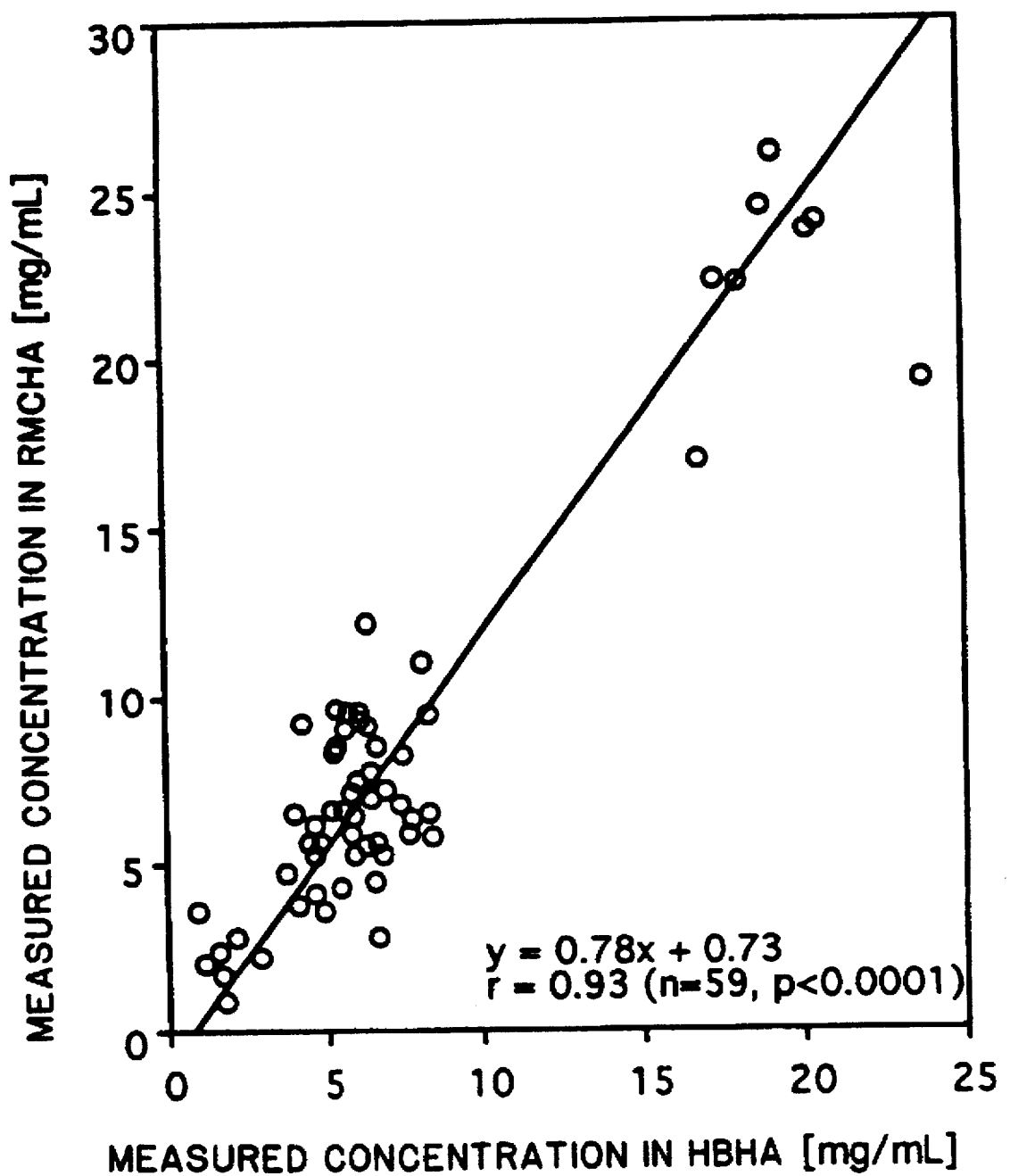
FIG. 14 is a graph depicting a correlation between human basophil histamine assay (HBHA) and rat mast cell histamine assay (RMCHA) results. Fifteen samples of rhuMAbE25 were each tested at two doses in both the HBHA and RMCHA for ability to inhibit ragweed-induced histamine release. The rhuMAbE25 concentrations of the samples were determined from the rhuMAbE25 standard curve of the respective assay. The recovered rhuMAbE25 concentrations (after correction for the dilution factors) were plotted. Simple regression analysis with a 95% confidence interval was performed using the StatView 4.0 program.
Figure 15A:
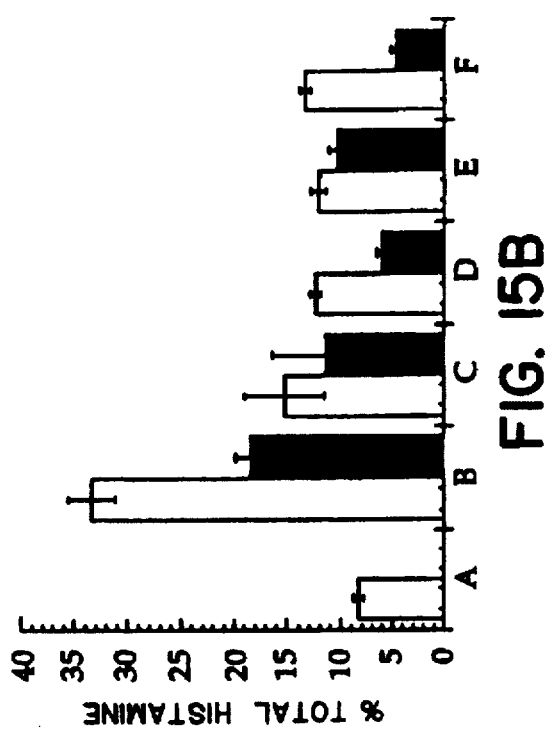
FIGS. 15A–15D disclose four graphs depicting the RMCHA screening of human plasma samples from allergic subjects against an allergen panel. RBL48 cells were seeded at 40,000 cells/well and cultured overnight at 37° C. in a 5% $CO_2$ incubator. Cells were separately sensitized with plasma samples isolated from four different allergic donors (P1, P2, P3 and P4) and then challenged with HRB (A), HRB and 0.1 µg/ml standardized mite (*D. farinae*) allergen (B), HRB and 0.1 µg/ml house dust mix allergen (C), HRB and 0.1 µg/ml ragweed antigens E-B and E-C (D), HRB and 0.1 µg/ml standardized cat pelt allergen (E), or HRB and 0.1 µg/ml *Alternaria tenius* allergen (F). The allergen-induced histamine release was determined as a percent of total cellular histamine for samples sensitized in the absence (open bar) or presence (filled bar) of 1 µg/ml rhuMAbE25. Each bar represents the mean of duplicate determinations.
Figure 15B:
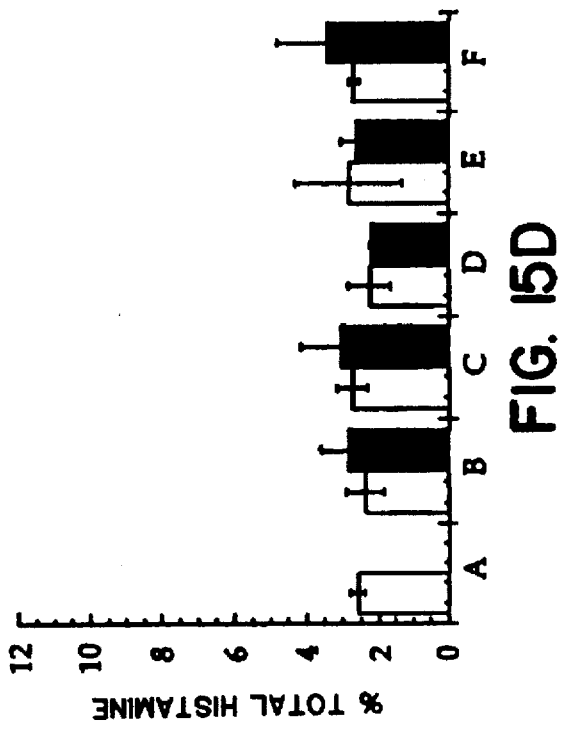
Figure 15C:
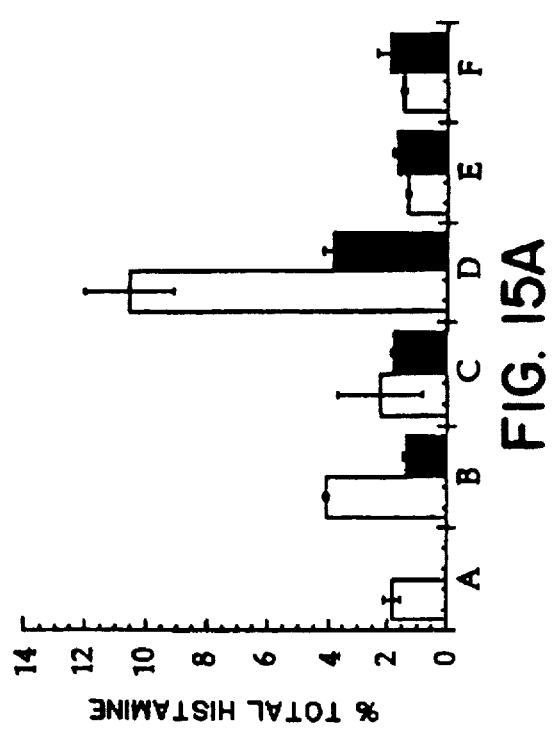
Figure 15D:
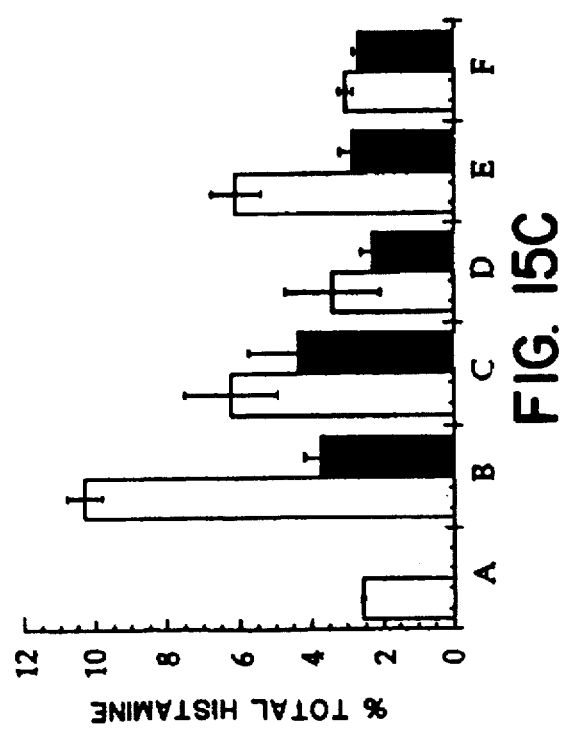

In evaluating the activity of 15 samples of rhuMAbE25, a good correlation was demonstrated between the RMCHA and the HBHA with a correlation coefficient of 0.93 (n=59, p<0.0001) (FIG. 14).

In addition, a panel of five allergens was used to challenge both naive donor blood basophils and RBL48 mast cells presensitized with IgE from each of the 8 human plasmas in the presence or absence of rhuMAbE25. A representative bar graph of four-individual plasma samples for the RMCHA is shown in FIGS. 15A–15D. When cells were sensitized with plasma sample one (P1), only mite (D. farinae) and ragweed allergen elicited histamine release significantly above the baseline (33% D2O/0.8% NaCl/1.3 mM $CaCl_2$/sIMDM (HRB)). However, preincubation with a second plasma sample (P2) caused significant histamine release when induced by mite (D. farinae), house dust, ragweed, cat pelt, and Alternaria tenuis allergens. Likewise, preincubation with a third plasma sample (P3) caused significant histamine release when induced by mite (D. farinae), house dust, ragweed, and cat pelt. In contrast none of the five allergens stimulated significant histamine release when cells were preincubated with a fourth plasma sample (P4). In all cases, allergen-induced histamine release could be blocked by 1 µg/mL of rhuMAbE25. Histamine release data obtained from the blood and cell assays performed on all eight plasma samples were analyzed with simple regression statistics. Table V below shows the correlation of the two assays for house dust allergen (r=0.84, p=0.0013, N=11), ragweed allergen (r=0.86, p=0.0133, N=7), cat pelt allergen (r=0.67, p=0.165, N=12), and all allergens (r=0.69, p=0.0001, N=37).

TABLE V

Correlation between HBHA and RMCHA in the allergen-induced histamine release

| Allergens | correlation coefficient (r) | N | p | slope |
|---|---|---|---|---|
| House dust | 0.84 | 11 | 0.0013 | 3.52 |
| Ragweed | 0.86 | 7 | 0.0133 | 1.07 |
| Cat pelt | 0.67 | 12 | 0.0165 | 3.93 |
| All allergens | 0.69 | 37 | 0.0001 | 2.03 | f. Effect of deuterium oxide ($D_2O$)

Figure 16:
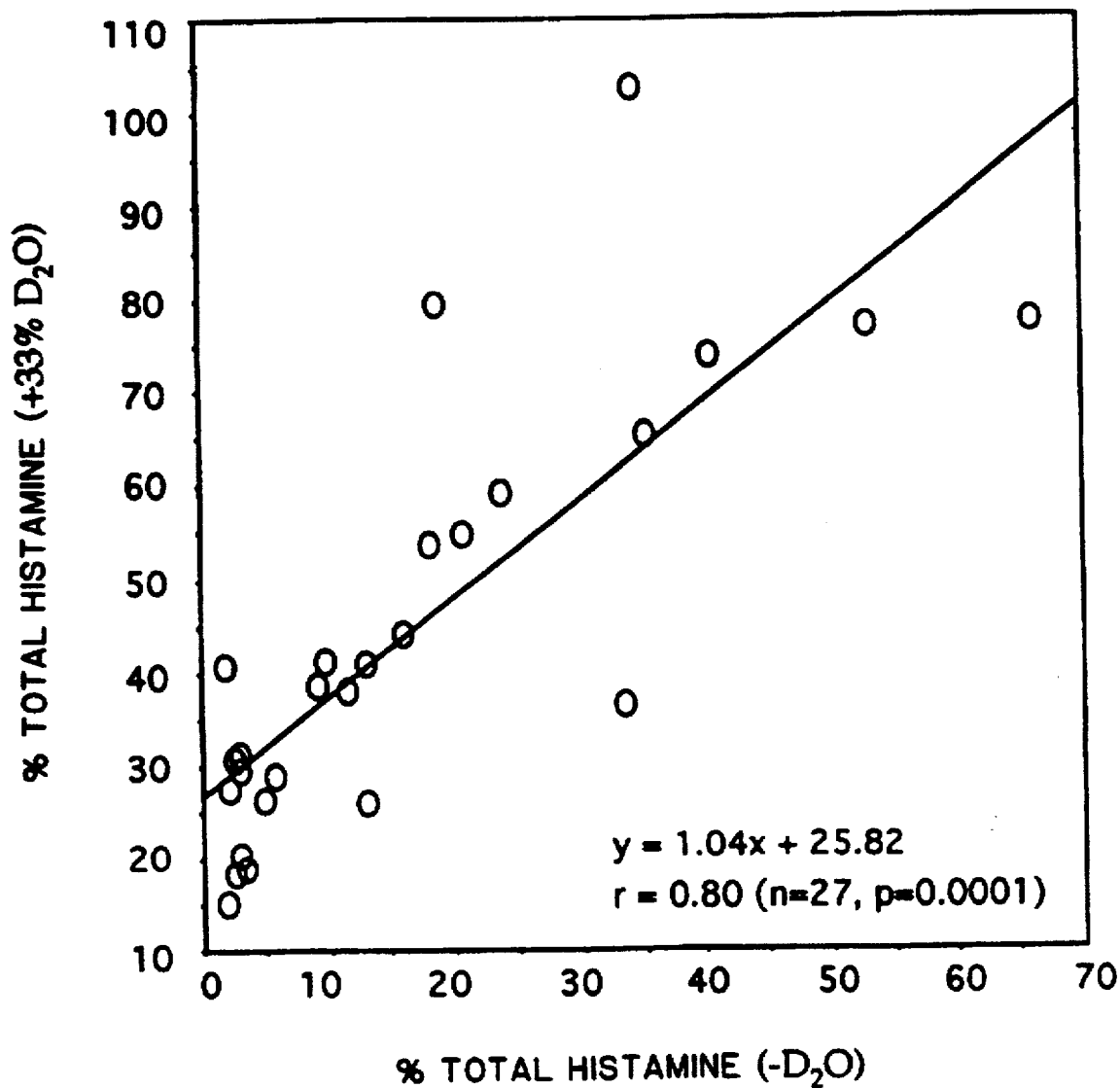
FIG. 16 is a graph depicting a comparison of histamine release induced by ragweed allergen and ragweed allergen/33% $D_2O$ in an HBHA assay. Donor's blood was incubated with 10% RSHP for 2 hours at 37° C. and then challenged with 0.1 µg/ml ragweed allergen in the presence or absence of 33% $D_2O$ for 30 minutes at 37° C. A total of 27 different naive donors were used. Each point represents the mean of duplicate determinations.

In order to study the effect of 33% $D_2O$, if any, in the HBHA system, a comparative study of ragweed-induced histamine release in the presence or absence of 33% $D_2O$ was performed. A total of 27 randomly selected healthy donors were recruited for the study. Donors' heparinized whole blood was pre-sensitized with 10% RSHP for 2 hr at 37° C. prior to challenge with 0.1 µg/mL (final concentration) of ragweed allergen for a further 30 min in the presence or absence of 33% $D_2O$. The concentration of histamine released into the supernatant was converted to percent total cellular histamine. Regression analysis shows a linear correlation (r=0.80, slope=1.04, p=0.0001) between ragweed- and ragweed/33% $D_2O$-induced histamine release (FIG. 16). The data indicate that the profile of enhanced histamine release in the presence of 33% $D_2O$ is proportional and comparable to ragweed challenge without $D_2O$.

Figure 17:
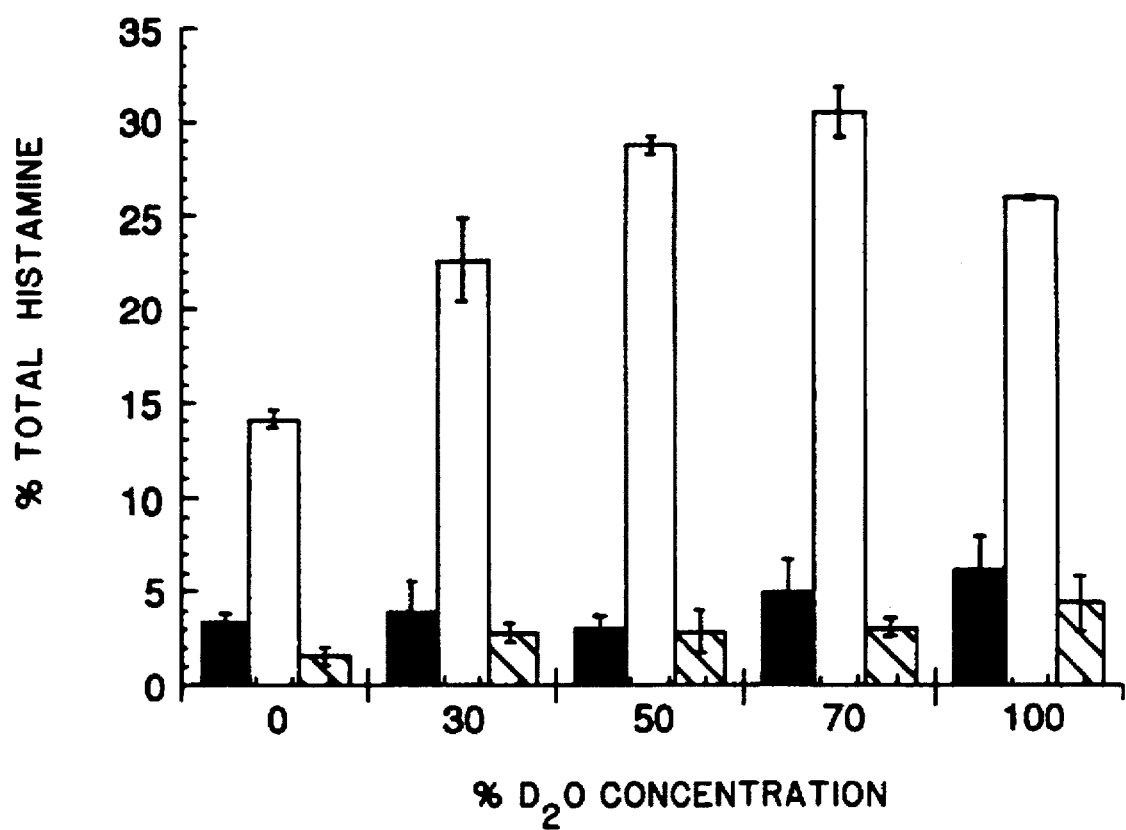
FIG. 17 is a graph depicting the effect of $D_2O$ on ragweed-induced histamine release in RBL48 cells. RBL48 cells were seeded at 40,000 cells/well and cultured overnight at 37° C. in a 5% $CO_2$ incubator. Cells were preincubated for 2 hours with sIMDM or sIMDM/10 µg/ml rhuMAbE25 in the presence of 10% (v/v) RSHP at 37° C. After 3 washes with sIMDM, cells were separately challenged with various concentrations of $D_2O$ (0%, 30%, 50%, 70%, 100%) in each of the following mixtures: (1) HRB (filled bar); (2) HRB and 0.1 µg/ml of ragweed allergen (open bar); and (3) HRB, 0.1 µg/ml of ragweed allergen, and 10 µg/ml rhuMAbE25 (hatched bar). Each point represents the mean of duplicate determinations.

The effect of $D_2O$ on the RMCHA was also examined. It was determined that $D_2O$ enhanced histamine release in RBL48 cells in a dose-dependent fashion reaching a maximal release at 50% $D_2O$ (FIG. 17). However, $D_2O$ neither stimulates histamine release by itself nor interferes with rhuMAbE25 inhibition of histamine release by RBL48 cells.

The effect of $D_2O$ on the pH of reagents used in these assays was investigated in order to determine whether the enhanced histamine release caused by $D_2O$ is not due to changes of pH. The pH of various reagents (2 mL) used in the HBHA (HBSS, HBSS+1% BSA, HBSS+1% BSA+ Blood+10% RSHP, HBSS+1% BSA+Blood+10% RSHP+ 33% D₂O, Blood, and 100% RSHP) and in the RMCHA (sIMDM, sIMDM+3 U/mL Sodium Heparin, and sIMDM+ 33% D₂O) were analyzed after 1 hr incubation at either ambient or 37° C. Each pH value shown in Table VI below represents the mean of triplicate determinations. As expected, the pH of the reagents becomes slightly acidic at 37° C. compared to that at ambient temperature. Although 33% D₂O causes a slight alkalization of blood reagent (at 37° C.) from pH of 7.20±0.01 to 7.34±0.01, it does not significantly change the pH of whole blood (pH 7.35±0.01) or the pH of the RMCHA reagents.

TABLE VI pH of various reagents for HBHA and RMCHA

| Reagents | pH Ambient | pH 37° C. |
| --- | --- | --- |
| HBSS | 7.20 ± 0.01 | 6.83 ± 0.01 |
| HBSS + 1% BSA | 7.18 ± 0.01 | 6.82 ± 0.01 |
| HBSS + 1% BSA + Blood + RSHP | 7.61 ± 0 | 7.20 ± 0.01 |
| HBSS + 1% BSA + Blood+ RSHP + D₂O | 7.75 ± 0 | 7.34 ± 0.01 |
| Blood | 7.51 ± 0.01 | 7.35 ± 0.01 |
| RSHP | 8.14 ± 0 | 7.95 ± 0.01 |
| sIMDM | 7.72 ± 0.03 | 7.44 ± 0.02 |
| sIMDM + Sodium Heparin | 7.73 ± 0.02 | 7.49 ± 0.01 |
| sIMDM + D₂O | 7.69 ± 0.01 | 7.42 ± 0.02 |

3. Discussion

A bioassay was developed to quantitate allergen-induced histamine release and rhuMAbE25 activity using a rat mast cell line (RBL48) transfected with the α-subunit of the human Fc$_ε$RI receptor. In the assay, RBL48 cells were sensitized with human plasma containing allergen specific IgE which binds to Fc$_ε$RI receptors expressed on the surface of these cells (FIG. 10). Subsequent challenge with ragweed allergen resulted in histamine release (FIG. 11) that was inhibited by the anti-IgE monoclonal antibody (rhuMAbE25) in a dose-dependent manner (FIG. 13). Since rhuMAbE25 can inhibit any allergen-induced histamine release, the format of this assay can be applied to all allergens. The assay can be modified by using a panel of allergens to screen human plasma samples for diagnosing IgE-mediated allergic conditions (FIGS. 15A–15D).

In developing the RMCHA, the effect of D₂O on histamine release was carefully investigated. As shown in FIG. 17, histamine release was not observed even when RBL48 cells were challenged with high concentrations (up to 100%) of D₂O. The data in FIG. 16 demonstrates a statistical significant correlation (r=0.80, n=27, p=0.0001) between histamine release induced by ragweed and ragweed/33% D₂O indicating that D₂O facilitates proportional histamine release in blood basophils. The presence of 33% D₂O appears to have no marked effect on the physiological pH of either the HBHA or the RMCFA reagent (Table VI).

The format of RMCHA may be readily modified to determine the effectiveness of rhuMAbE25 or other IgE antagonists in inhibiting histamine release induced by a variety of allergens as shown in. FIGS. 15A–15D. Histamine release above baseline (HRB) is an indication of the presence of allergen specific IgE in the plasma. The data obtained herein indicates that plasma sample one (P1) contains IgE specific to mite (*D. farinae*) and ragweed since these two allergens stimulated histamine release significantly above baseline. Likewise, plasma sample two (P2) contains IgE specific to mite (*D. farinae*), house dust mix, ragweed, cat pelt, and *Alternaria tenuis*; plasma sample three (P3) contains IgE specific to mite (*D. farinae*), house dust mix, ragweed, and cat pelt; and plasma sample four (P4) contains no IgE specific to any of these five allergens. Similar profiles of histamine release were obtained when these allergens were used to challenge blood basophils in the HBHA. Since the RMCHA correlates well with the HBHA in evaluating the biological activities of fifteen humanized anti-IgE monoclonal antibodies (FIG. 14) and in histamine release induced by various allergens (Table VI), it can be used as an additional tool of diagnosing IgE-mediated allergies.

Since several studies have clearly demonstrated that IgE levels correlate with allergic disease (Bahna, *Ann. Allergy* 62: 471–475 (1989); Mascia et al., *Ann. Allergy* 62: 311–318 (1989); Platts-Mills, *Am. Rev. Respir. Dis.* 145: S44–S47 (1992), this RMCHA can be used to study and explore IgE-mediated pathway as well as to predict the likely efficacy of immunotherapy aimed at blocking of binding of IgE to Fc$_ε$RI.

We claim:

1. A method for diagnosis of allergic disease in a patient comprising
   (a) comparing release of a pharmacological mediator in a reaction mixture with release of the pharmacological mediator in a blocked reaction mixture, wherein
      (1) the reaction mixture and the blocked reaction mixture comprise genetically engineered cells that are the progeny of a common parent cell selected from the group consisting of: any mast cell host genetically engineered to display surface expression of a FcεRI α-subunit that is capable of mediating the host cell's release of the pharmacological mediator upon induction by patient serum IgE and allergen, and any basophil cell host genetically engineered to display surface expression of a FcεRI α-subunit that is capable of mediating the host cell's release of the pharmacological mediator upon induction by patient serum IgE and allergen;
      (2) the reaction mixture and the blocked reaction mixture each further comprises a portion of a single serum sample from the patient, the presence or absence in the serum sample of IgE specific for an allergen of interest being theretofore unknown;
      (3) the blocked reaction mixture further comprises an IgE antagonist selected from the group consisting of anti-IgE antibodies, antigen binding fragments of anti-IgE antibodies, soluble FcεRI receptor, and IgE variant capable of competing with IgE for binding to FcεRI receptor, said IgE variants having a reduced ability to sensitize immune cells; and
      (4) both the reaction mixture and the blocked reaction mixture are admixed with the allergen; and
   (b) determining, based on the comparison in step (a), the presence or absence in the serum sample of IgE specific for the allergen.

2. The method of claim 1 wherein the genetically engineered cells are genetically engineered mast cells.

3. The method of claim 2 wherein the genetically engineered mast cells are genetically engineered rodent mast cells.

4. The method of claim 3 wherein the genetically engineered rodent mast cells are genetically engineered rat mast cells.

5. The method of claim 1 wherein the Fc$_ε$RI α-subunit is derived from the animal species of the patient.

6. The method of claim 1 wherein the patient is human.

7. The method of claim 1 wherein the $Fc_\epsilon RI$ α-subunit is derived from a human source.

8. The method of claim 1 wherein the $Fc_\epsilon RI$ α-subunit is heterologous to the genetically engineered cells.

9. The method of claim 1 wherein the IgE antagonist is an anti-IgE antibody or antigen binding fragment thereof.

10. The method of claim 9 wherein the anti-IgE antibody is a monoclonal anti-IgB antibody.

11. The method of claim 1 wherein the IgE antagonist is an IgE variant.

12. The method of claim 1 wherein the IgE antagonist is a soluble $Fc_\epsilon RI$ receptor.

13. The method of claim 1 wherein the genetically engineered cells in the blocked reaction mixture are first admixed with the IgE antagonist and then admixed with the serum sample from the patient.

14. The method of claim 1 wherein the serum sample in the blocked reaction mixture is first admixed with the IgE antagonist and then admixed with the genetically engineered cells.

15. The method of claim 1 wherein the pharmacological mediator is histamine.

* * * * *